US012642280B2

(12) United States Patent
Geng

(10) Patent No.: US 12,642,280 B2
(45) Date of Patent: Jun. 2, 2026

(54) YEAST AND LACTIC ACID BACTERIA COMBINATION

(71) Applicant: Mingzhiyuan (Hangzhou) Biological Technology Co., Ltd, Hangzhou (CN)

(72) Inventor: Shengli Geng, Hangzhou (CN)

( * ) Notice: Subject to any disclaimer, the term of this patent is extended or adjusted under 35 U.S.C. 154(b) by 286 days.

(21) Appl. No.: 17/965,723

(22) Filed: Oct. 13, 2022

(65) Prior Publication Data

US 2023/0120822 A1 Apr. 20, 2023

(30) Foreign Application Priority Data

Oct. 14, 2021 (CN) .......................... 202111198135.X

(51) Int. Cl.
| | |
|---|---|
| *A23B 7/155* | (2006.01) |
| *A23B 4/22* | (2006.01) |
| *C12N 1/165* | (2026.01) |
| *C12N 1/205* | (2026.01) |
| *C12R 1/01* | (2006.01) |
| *C12R 1/225* | (2006.01) |
| *C12R 1/72* | (2006.01) |

(52) U.S. Cl.
CPC ................ *A23B 7/155* (2013.01); *A23B 4/22* (2013.01); *C12N 1/165* (2021.05); *C12N 1/205* (2021.05); *A23V 2002/00* (2013.01); *C12R 2001/01* (2021.05); *C12R 2001/225* (2021.05); *C12R 2001/72* (2021.05)

(58) Field of Classification Search
None
See application file for complete search history.

(56) References Cited

FOREIGN PATENT DOCUMENTS

JP 2003245062 * 9/2003

OTHER PUBLICATIONS

Geng WO 2018161361 A1 Machine Translation 4 pages (Year: 2018).*

* cited by examiner

*Primary Examiner* — Felicia C Turner

(57) ABSTRACT

The invention discloses a yeast and lactic acid bacteria combination, comprising *Saccharomyces* and lactic acid bacteria; wherein the *Saccharomyces* comprises *Candida ethanolica* B-JJ1, and the lactic acid bacteria comprise at least one of *Lentilactobacillus buchneri* B-JR1, *Lactobacillus paracasei* B-JR2, *Lactobacillus zeae* B-JR4, *Lactobacillus plantarum* B-JR5 and *Lactobacillus chiayiensis* B-JR6. The yeast and lactic acid bacteria combination is obtained by the processes of inoculum extraction, strain inoculation, combined bacteria optimization and combined bacteria domestication. The fermentation of the yeast and lactic acid bacteria combination provided by the invention can be adopted to prepare bio-enzyme preparation. And the prepared bio-enzyme preparation can be adopted to prepare natural, green, additive-free preservatives with strong anti-oxidant properties that maintain the activity of plant and animal cells.

2 Claims, 8 Drawing Sheets

Top: no enzymes, glycated, viscous

Bottom: Enzymatic, unglycated (a)                                    (b)

(a)                                    (b)

(a)                                    (b)

(a)                                        (b)

(a)                                        (b)

(a)                                        (b)

(a)

(b)                                        (c)

(a)

(b)                                    (c)

(a)                                    (b)

(a)                                    (b)

(a)　　　　　　　　　　　　　　　(b)

Top: no enzymes, glycated, viscous

Bottom: Enzymatic, unglycated (a)                  (b)

YEAST AND LACTIC ACID BACTERIA COMBINATION

TECHNICAL FIELD

The invention relates to the technical field of microbial applications, in particular to a yeast and lactic acid bacteria combination.

BACKGROUND

Combined flora (also known as combined microbial community or mixed flora) usually refers to a microbial ecosystem composed of two or more artificially selected superior cultures, and where the microorganisms have the characteristics of mutual nutritional benefits, complementary advantages, ecological balance, strong survivability and adaptability. Through skillfully combination of different bacteria cultures, it can make better use of performance advantage compared to the single culture of bacteria.

Lactic acid bacteria is a group of bacteria that produce large amounts of lactic acid by fermenting sugars, and can be morphologically divided into cocci and bacilli. Lactic acid bacteria are gram positive bacteria, and facultative anaerobes or anaerobic bacteria that can be well-grown in the environment lacking of oxygen. They are widely distributed in nature and are found in the intestinal tract of humans, livestock and poultry, and are also contained in many foods, materials and in a few clinical samples. With the exception of the minority of lactic acid bacteria, most of them are essential flora for physiological functions in humans and animals. Yeast is a typical group of unicellular microorganisms with a simple structure and belongs to funguses. Because yeast has the advantages of large size, high protein content and high omnivory, with easy separation, convenient cultivation, multiple metabolites and wide comprehensive use, it is used in the industry nowadays not only for brewing but also for the production of glycerine, organic acids and enzyme preparations. Both lactic acid bacteria and yeast are beneficial microorganisms for human beings and with similar growth conditions, which generates the symbiotic basis.

SUMMARY OF THE INVENTION

With the above background of the prior art, the invention intended to provide a yeast and lactic acid bacteria combination with the preparation method and application thereof, and the yeast and lactic acid bacteria combination is obtained by the processes of inoculum extraction, strain inoculation, combined bacteria optimization and combined bacteria domestication. The fermentation of the yeast and lactic acid bacteria combination provided by the invention can be adopted to prepare bio-enzyme preparation; and the prepared bio-enzyme preparation can be adopted to prepare natural, green, additive-free preservatives with strong antioxidant properties that maintain the activity of plant and animal cells.

The technical solutions provided by the invention are as follows:

A yeast and lactic acid bacteria combination comprises *Candida ethanolica* B-JJ1, *Lentilactobacillus buchneri* B-JR1, *Lactobacillus paracasei* B-JR2, *Lactobacillus zeae* B-JR4, *Lactobacillus plantarum* B-JR5 and *Lactobacillus chiayiensis* B-JR6;

The *Candida ethanolica* B-JJ1 with the deposit number: CCTCC NO: M2021136;

The *Lentilactobacillus buchneri* B-JR1 with the deposit number: CCTCC NO: M2021132;

The *Lactobacillus paracasei* B-JR2 with the deposit number: CCTCC NO: M2021133;

The *Lactobacillus zeae* (*Lactobacillus corni*) B-JR4 with the deposit number: CCTCC NO: M2021135;

The *Lactobacillus plantarum* B-JR5 with the deposit number: CCTCC NO: M2021501;

The *Lactobacillus chiayiensis* B-JR6 with the deposit number: CCTCC NO: M2021502.

Further, the solution comprises yeasts and lactic acid bacteria; wherein the yeasts comprise *Candida ethanolica* B-JJ1, and the lactic acid bacteria are be composed of *Lentilactobacillus buchneri* B-JR1, *Lactobacillus paracasei* B-JR2, *Lactobacillus zeae* B-JR4, *Lactobacillus plantarum* B-JR5 and *Lactobacillus chiayiensis* B-JR6.

1. The invention also provides a method for cultivating above yeast and lactic acid bacteria combination, comprising the following steps:

(1) Inoculum extraction: taking the pit mud fermentation from the Chinese liquor brewing mud pit, adding sterile water to the pit mud fermentation in accordance with the weight ratio, and letting stand for use after mixing sufficiently;

(2) Culture medium preparation: the medium is prepared with mashed potato powder, wheat germ and glutinous rice as the main ingredients for preparation; taking raw materials in accordance with the weight ratio and adding water and stirring sufficiently; and after steam distillation until the granular swelling, the culture medium can be placed in a sterile container for heat dissipation; and cooling the temperature of medium to a certain temperature for use;

(3) Strain inoculation: the pit mud fermentation in the step (1) and the prepared medium in the step (2) are mixed evenly according to the weight ratio, and then placed in an aseptic conditions for constant temperature aerobic cultivation;

(4) Anaerobic breeding: when the medium in the step (3) appears white or milky white bacterial plaque evenly distributed, and there is a wet and sticky feeling and light fermentation fragrance when pushing the surface aside; the medium will be packed in separate bags and the medium will continue to ferment at a constant temperature after being packed in separate bags;

(5) Obtain facultative anaerobes yeast and lactic acid bacteria combination: after depleting the residual oxygen in the bag, the medium in the bag appears agglomeration in vacuum with white, creamy white bacterial plaque and covered with bacterial film;

(6) Facultative anaerobes yeast and lactic acid bacteria combination optimization: the medium packed in the bag in the step (5) will continue anaerobic fermentation to allow facultative anaerobes bacteria to continue to proliferate and further exclude aerobic bacteria, until the white, milky white bacterial film completely covers the medium, to complete occupancy and saturated fermentation;

(7) Sampling and testing to identify the obtained symbiotic colonies: testing the activity of the combined bacteria in the step (6), and when the average value of viable yeast is $6.4 \times 10^4$ cfu/ml or more; the average value of viable lactic acid bacteria is $4 \times 10^8$ cfu/ml or more, the first generation of yeast and lactic acid bacteria combination is obtained;

(8) Combined bacteria domestication: mixing the medium in the step (2) with the first generation of yeast and lactic acid bacteria combination in the step (7), and spraying sterile water or steamer water cooled to 37° C. until moistened to wet and scattered, with water dripping out when hold by hand; then activate it aerobically until the surface of the medium appears white or milky white bacterial plaque evenly distributed, and there is a wet and sticky feeling and light fermentation fragrance when pushing the surface aside; then providing the mixed medium into the closed environment for continued fermentation, until the gradual depletion of surrounding oxygen and entering into anaerobic fermentation; the combined bacteria domestication can be regarded as finished when processing anaerobic fermentation until the colony yeast and lactic acid bacteria combination grows vigorously.

2. Further, the above method for cultivating above yeast and lactic acid bacteria combination, comprising the following steps:

(1) Inoculum extraction: taking the pit mud fermentation from the Chinese liquor brewing mud pit, adding sterile water with the temperature of 35-38° C. to the pit mud fermentation in accordance with the weight ratio of 2:1, and letting stand for use after mixing sufficiently;

(2) Culture medium preparation: the medium is prepared with mashed potato powder, wheat germ and glutinous rice as the main ingredients for preparation; taking raw materials in accordance with the weight ratio of 1:1 and adding water and stirring sufficiently; and after steam distillation for 40 minutes until the granular swelling, the culture medium can be placed in a sterile container for heat dissipation; and cooling the temperature of medium to below 45° C. for use;

Further, the above medium further comprises sorghum rice and buckwheat.

Further, the ratio of each ingredient of the medium is as follows:

4 parts of sorghum rice, 3 parts of mashed potato powder, 1 part of wheat germ, 1 part of buckwheat, 1 part of glutinous rice.

Further, 5% of sorghum rice and buckwheat can be replaced by sugar.

(3) Strain inoculation: the pit mud fermentation in the step (1) and the prepared medium in the step (2) are mixed evenly according to the weight ratio of 1:2, and then placed in an aseptic conditions with the temperature above 26° C. for constant temperature aerobic cultivation for over 45 hours and it is necessary to pay attention to the medium changes during this process;

(4) Anaerobic breeding: when the medium in the step (3) appears white or milky white bacterial plaque evenly distributed, and there is a wet and sticky feeling and light fermentation fragrance when pushing the surface aside; the medium will be packed in separate bags according to 1-5 kg respectively and the medium will continue to ferment at a constant temperature of 37° C. after being packed in separate bags;

(5) Obtain facultative anaerobes yeast and lactic acid bacteria combination: after depleting the residual oxygen in the bag, the medium in the bag appears agglomeration in vacuum with white, creamy white bacterial plaque and covered with bacterial film. When covered by the bacterial film, a variety of aerobic bacteria of *Aspergillus* and *Mucor* species will enter into apoptosis, the main survival with slow proliferation is facultative anaerobe yeast and lactic acid bacteria combination;

(6) Facultative anaerobes yeast and lactic acid bacteria combination optimization: the medium packed in the bag in the step (5) will continue anaerobic fermentation to allow facultative anaerobes bacteria to continue to proliferate and further exclude aerobic bacteria, until the white, milky white bacterial film completely covers the medium, to complete occupancy and saturated fermentation;

(7) Sampling and testing to identify the obtained symbiotic colonies: testing the activity of the combined bacteria in the step (6), and when the average value of viable yeast is $6.4 \times 10^4$ cfu/ml or more; the average value of viable lactic acid bacteria is $4 \times 10^8$ cfu/ml or more, the first generation of yeast and lactic acid bacteria combination is obtained;

(8) Combined bacteria domestication: mixing the medium in the step (2) with the first generation of yeast and lactic acid bacteria combination in the step (7) according to the weight ratio of 1:1, and spraying sterile water or steamer water cooled to 37° C. until moistened to wet and scattered, with water dripping out when hold by hand; then placing it in sterile condition with the temperature above 26° C. for more than 48 hours of aerobic activation, until the surface of the medium appears white or milky white bacterial plaque evenly distributed, and there is a wet and sticky feeling and light fermentation fragrance when pushing the surface aside; then providing the mixed medium into the closed environment for continued fermentation, until the gradual depletion of surrounding oxygen and entering into anaerobic fermentation; the combined bacteria domestication can be regarded as finished when processing anaerobic fermentation for 20-30 days until the colony yeast and lactic acid bacteria combination grows vigorously.

Further, the method further comprises the following steps:

(9) Packaging of the combined bacteria: the domesticated yeast and lactic acid bacteria combination in the step (8) are vacuum packed according to 5-10 kg/bag.

Further, the average value of viable bacteria in the yeast and lactic acid bacteria combination in step (9) after packaging is more than $6.4 \times 10^4$ cfu/ml, and the average value of viable lactic acid bacteria is more than $4 \times 10^8$ cfu/ml.

The invention also provides a method for preparing the bio-enzyme preparation, wherein the bio-enzyme preparation comprises the fermentation products of the above yeast and lactic acid bacteria combination.

3. Further, the method for preparing the bio-enzyme preparation, wherein comprises the following steps:

(1) Selecting the yeast and lactic acid bacteria combination according to the claim 1 as the culture;

(2) The preparation and inoculation of the culture medium: the medium is prepared with mashed potato powder, wheat germ and glutinous rice as the main ingredients; the medium is steamed after adding water and stirring evenly, and the preparation of the medium has been completed when the temperature of the medium is cooled to below 45° C. in the aseptic conditions; homogeneously mixing the prepared medium with the culture;

(3) Adjusting the humidity of the culture medium after inoculation in step (2) to ensure that the medium remain water seeping when hold by hand and the whole medium is kept moist and breathable;

(4) Processing the aerobic fermentation of the medium in step (3) until the medium uniformly appears white and milky white bacterial plaque to be visible with the naked eye, and then transferring the medium into the fermenter; to close all channels of the fermenter to enable the medium fermentations into the tank to continue aerobic culture in the tank until the oxygen in the tank is depleted and enters the anaerobic fermentation state;

(5) When there is no pressure change in the fermenter, the solid-state fermentation enters into saturation fermentation, and there is a strong fermentation fragrance when opening the tank, with abundant mycelium covering the surface of the solid medium to be visible with the naked eye; taking the fermentation products for testing, and the total number of viable yeast is $6.4 \times 10^4$-$5.9 \times 10^5$ cfu/ml; the total number of viable lactic acid bacteria is $4 \times 10^8$-$5.1 \times 10^9$ cfu/ml; and at this time the solid fermentation process has reached saturation point, and then enters the liquid fermentation stage;

(6) Adding the solid fermentation in the step (5) to sterile water and stirring thoroughly to dilute the metabolic substrate in the solid fermentation process, and carrying out aerobic activation and cultivation until the surface of the liquid ferment is densely covered with white or milky white bacterial plaque; to close all channels of the fermenter and again allow the fermentation to gradually deplete oxygen and enter into the anaerobic fermentation process;

(7) When the bacterial plaque on the surface of the liquid fermentation in step (6) is in folding state, the middle and upper layers of clear liquid appear golden yellow, clear and transparent, and the solid fermentation to liquid fermentation process is regarded as full complement, when the bottom layer of solid fermentation and the middle layer of liquid are clearly layered and not sticky, and the fermentation product obtained is the bio-enzyme preparation.

Further, the method 2 comprises the following steps:

(8) Heating the fermentation substrate obtained in step (7) and extracting the supernatant of the ferment, to obtain the inactivated bio-enzyme preparation.

The invention also provides the application of the above bio-enzyme preparation, which can be adopted to prepare the biological preservatives.

Further, the biological preservative can be applied to preserving vegetables, fruits, and fresh or dried meat.

Further, the biological preservatives may be adopted in the preparation of human or animal body specimens.

Compared to the prior art, the technical solution provided by the invention has the following technical advantages and beneficial effects:

(1) The invention adopts the process of inoculation, breeding, optimization and domestication of the combined bacteria, to cultivate the yeast and lactic acid bacteria with strong symbiotic ability and good stability; and the cultivated combined bacteria have high activity, which can be purified and separated according to the actual requirements, and then mixing and preparing the combined bacteria with different properties;

(2) The combined bacteria provided by the invention has experienced complex biochemical reactions through fermentation, and the obtained fermentation products are abundant in various active groups such as amino acid residues, amides, coenzymes, lactic acid and linoleic acid, which can be adopted to prepare bio-enzyme preparations with abundant nutrition, and the bio-enzyme preparations prepared by the invention can be adopted to prepare preservatives;

(3) The preservatives prepared by the invention not only has various amino acids, various enzymes, enzyme precursors and other nutritional components that can maintain the cellular activity of animal and plant tissues and can repair the defective cells, but also can delay the glycation process of the organism through the inhibition of a-amylase activity and can kill microorganisms such as putrefactive mould, with strong antioxidant, preservative and preservative effects;

(4) The preservatives prepared by the biol-enzyme preparation provided by the invention is natural, safe and efficient without any additives, which can be adopted not only for preserving fresh plants or meat, making plant and animal cells remain active for a long time and prolonging their preservation time, but also for preserving dried meat to prevent oxidation and discoloration.

BRIEF DESCRIPTION OF THE DRAWINGS

To make the technical solutions in the embodiments provided by the invention or in the prior art more comprehensible, a brief description of the drawings required in the description of the embodiments or prior art is given below, and it is obvious that drawings in the following description are only some of the embodiment provided by the invention and not the limitations of the scope of the disclosure. Other drawings can be obtained on the basis of these drawings without creative work by those of ordinary skill in the art.

Figure 1:
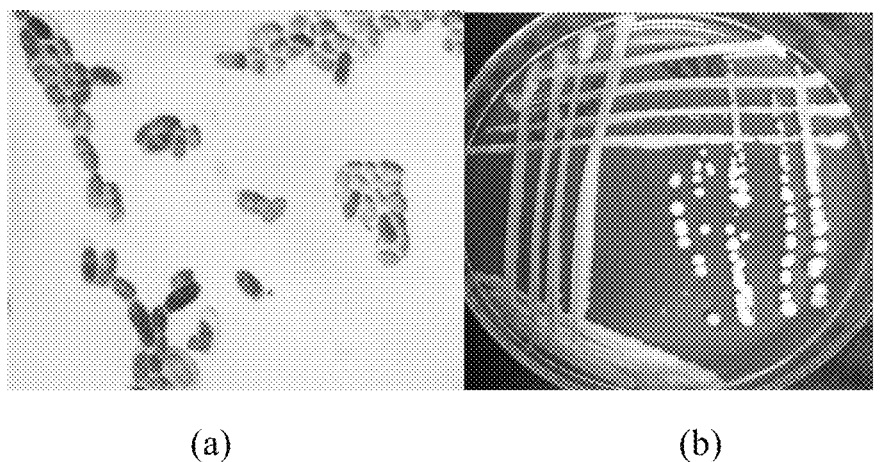
FIG. 1 is a photograph showing the morphological characteristics of the strain of *Candida ethanolica* B-JJ1 provided by the invention; wherein (a) is the microscopic photograph taken by light microscope (400×); (b) is a frontal plate photograph.
Figure 2:
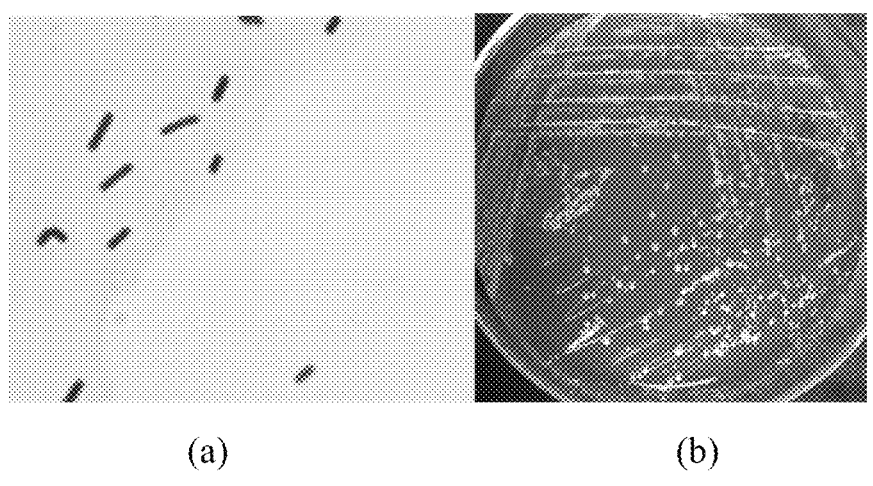
FIG. 2 is a photograph showing the morphological characteristics of the strain of *Lentilactobacillus buchneri* B-JR1 provided by the invention; wherein (a) is the microscopic photograph taken by light microscope (1000×); (b) is a frontal plate photograph.
Figure 3:
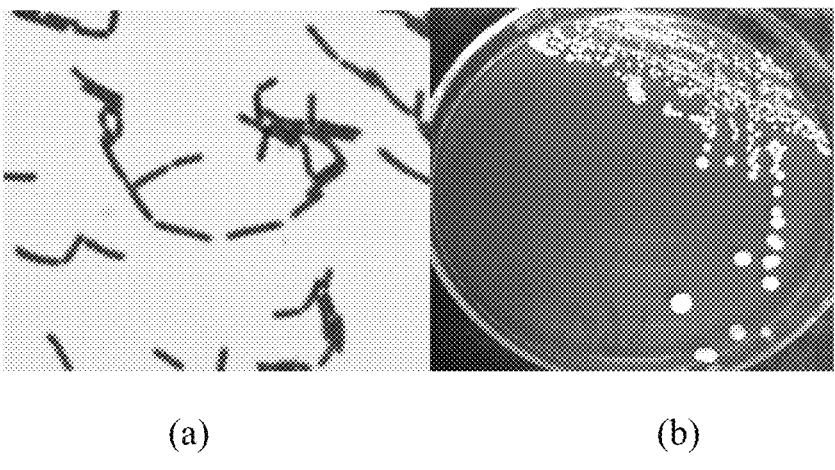
FIG. 3 is a photograph showing the morphological characteristics of the strain of *Lactobacillus paracasei* B-JR2 provided by the invention; wherein (a) is the microscopic photograph taken by light microscope (1000×); (b) is a frontal plate photograph.
Figure 4:
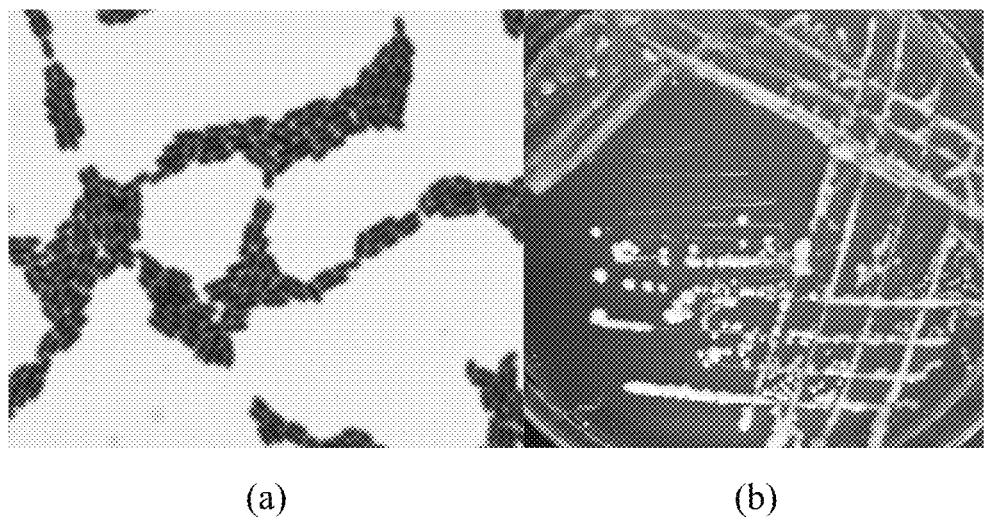
FIG. 4 is a photograph showing the morphological characteristics of the strain of *Lactobacillus zeae* B-JR4 provided by the invention; wherein (a) is the microscopic photograph taken by light microscope (1000×); (b) is a frontal plate photograph.
Figure 5:
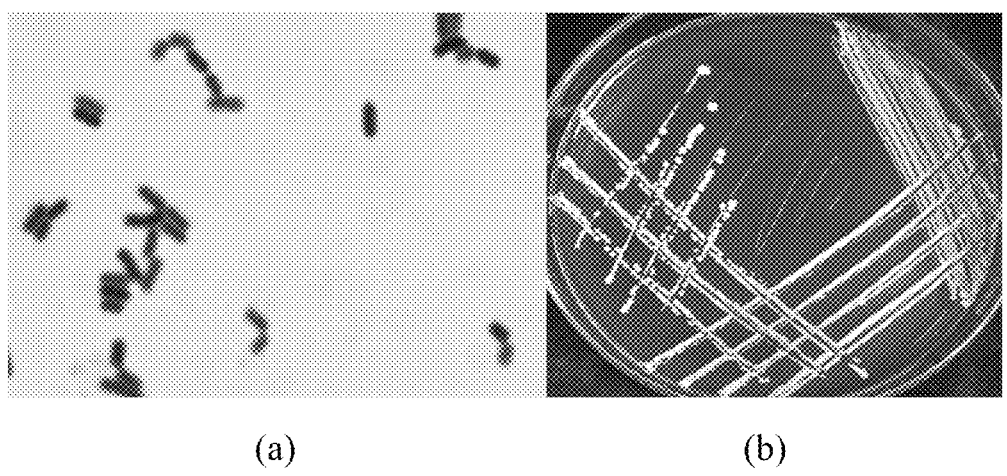
FIG. 5 is a photograph showing the morphological characteristics of the strain of *Lactobacillus plantarum* B-JR5 provided by the invention; wherein (a) is the microscopic photograph taken by light microscope (1000×); (b) is a frontal plate photograph.
Figure 6:
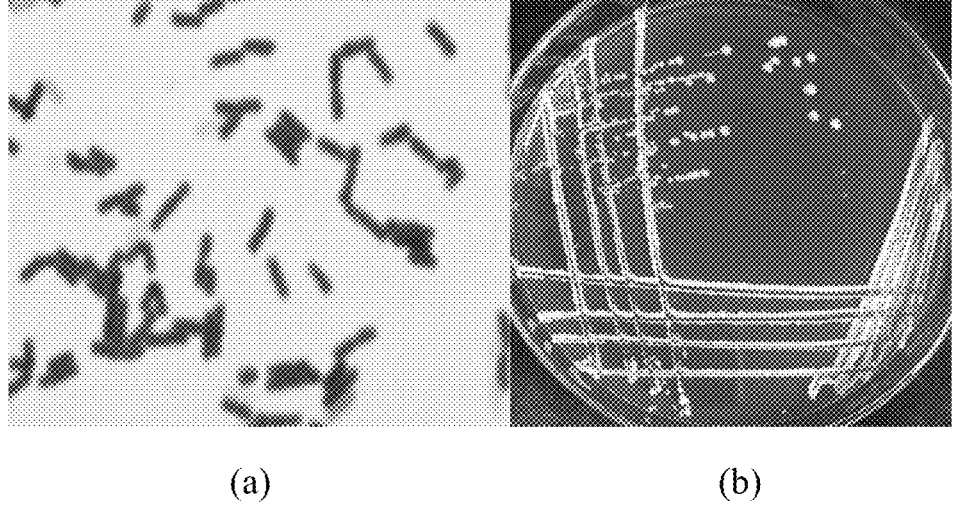
FIG. 6 is a photograph showing the morphological characteristics of the strain of *Lactobacillus chiayiensis* B-JR6 provided by the invention; wherein (a) is the microscopic photograph taken by light microscope (1000×); (b) is a frontal plate photograph.

The *Candida ethanolica* B-JJ1 provided by the invention with the deposit number: CCTCC NO: M2021136; the collection date is Jan. 21, 2021; the collection institution is China Center for Type Culture Collection (CCTCC); the deposit site is Wuhan University.

The *Lentilactobacillus buchneri* B-JR1 provided by the invention with the deposit number: CCTCC NO: M2021132; the collection date is Jan. 21, 2021; the collection institution is China Center for Type Culture Collection (CCTCC); the deposit site is Wuhan University.

The *Lactobacillus paracasei* B-JR2 provided by the invention with the deposit number: CCTCC NO: M2021133; the collection date is Jan. 21, 2021; the collection institution is China Center for Type Culture Collection (CCTCC); the deposit site is Wuhan University.

The *Lactobacillus zeae* B-JR4 provided by the invention with the deposit number: CCTCC NO: M2021135; the collection date is Jan. 21, 2021; the collection institution is China Center for Type Culture Collection (CCTCC); the deposit site is Wuhan University.

The *Lactobacillus plantarum* B-JR5 provided by the invention with the deposit number: CCTCC NO: M2021501; the collection date is May 7, 2021; the collection institution is China Center for Type Culture Collection (CCTCC); the deposit site is Wuhan University.

The *Lactobacillus chiayiensis* B-JR6 provided by the invention with the deposit number: CCTCC NO: M2021502; the collection date is May 7, 2021; the collection institution is China Center for Type Culture Collection (CCTCC); the deposit site is Wuhan University.

DESCRIPTION OF EMBODIMENTS

To make the purpose, technical solutions and advantages of the embodiments provided by the invention more comprehensible, a further description of the invention is given below in combination with the attached drawings and embodiments, and the embodiments are exemplary and not the limitations of the scope of the disclosure. It is clear that the embodiments in the following description are a part of the embodiments provided by the invention instead of all of them. Based on the embodiments in the invention, all other embodiments obtained by those of ordinary skill in the art without making creative effort shall fall within the scope of protection of the invention.

A further description of the invention is given below in combination with the attached drawings and embodiments.

Embodiment 1

A yeast and lactic acid bacteria combination, the cultivation method comprises the following steps:

(1) Inoculum extraction: taking the pit mud fermentation from the Chinese liquor brewing mud pit form the different orientation, and the different directions mentioned refer to the east, south, west and north, the pit walls and the bottom of the pit; adding sterile water with the temperature of 35-38° C. to the pit mud fermentation in accordance with the weight ratio of 2:1, and letting stand for use after mixing sufficiently; the brewing pit in this embodiment is a traditional brewing pit of Chinese liquor in the Yaowan ancient town in northern Jiangsu Province;

(2) Culture medium preparation: taking 4 parts of sorghum rice, 3 parts of mashed potato powder, 1 part of wheat germ, 1 part of buckwheat and 1 part of glutinous rice as the main ingredients for preparation; taking raw materials in accordance with the weight ratio of 1:1 and adding water and stirring sufficiently; and after steam distillation for 40 minutes until the granular swelling, the culture medium can be placed in a sterile container for heat dissipation; and cooling the temperature of medium to below 45° C. for use;

(3) Strain inoculation: the pit mud fermentation in the step (1) and the prepared medium in the step (2) are mixed evenly according to the weight ratio of 1:2, and then placed in an aseptic conditions with the temperature above 26° C. for constant temperature aerobic cultivation for over 45 hours and it is necessary to pay attention to the medium changes during this process;

(4) Anaerobic breeding: when the medium in the step (3) appears white or milky white bacterial plaque evenly distributed, and there is a wet and sticky feeling and light fermentation fragrance when pushing the surface aside; the medium will be packed in separate bags according to 1-5 kg respectively and the medium will continue to ferment at a constant temperature of 37° C. after being packed in separate bags;

In this step, due to the previous culture with a large number of aerobic colonies, there will be the output of gas after sealing the bag, therefore, it is necessary to pay attention to the appropriate time to release the gas and reduce the pressure.

(5) Obtain facultative anaerobes yeast and lactic acid bacteria combination: after depleting the residual oxygen in the bag, the medium in the bag appears agglomeration in vacuum with white, creamy white bacterial plaque and covered with bacterial film. When covered by the bacterial film, a variety of aerobic bacteria of *Aspergillus* and *Mucor* species will enter into apoptosis, the main survival with slow proliferation is facultative anaerobe yeast and lactic acid bacteria combination;

(6) Facultative anaerobes yeast and lactic acid bacteria combination optimization: the medium packed in the bag in the step (5) will continue anaerobic fermentation to allow facultative anaerobes bacteria to continue to proliferate and further exclude aerobic bacteria, until the white, milky white bacterial film completely covers the medium, to complete occupancy and saturated fermentation; the aerobic bacteria have almost no survival conditions at this time (there may exist a very few fungal spores but they will be completely eliminated due to the suppression of community dominance and subsequent processes); at the same time, the facultative anaerobe bacteria are gradually entering a dormant state and waiting for recovery;

(7) Sampling and testing to identify the obtained symbiotic colonies: testing the activity of the combined bacteria in the step (6), and when the average value of viable yeast is 6.4×10$^4$ cfu/ml or more; the average value of viable lactic acid bacteria is 4×10$^8$ cfu/ml or more, the first generation of yeast and lactic acid bacteria combination is obtained;

In this embodiment, the maximum value of viable yeast is 3.1×10$^5$ cfu/ml and the maximum value of viable lactic acid bacteria is 1.2×10$^9$ cfu/ml.

(8) Combined bacteria domestication: due to the acquisition of the combined colonies, out of the complementary of the large communities of *Aspergillus* and *Mucor*, forming symbiotic adaptations between new small communities, adaptations to the medium and adaptations to changes in the survival environment such as the conversion of aerobic and anaerobic environments, therefore it is necessary to domesticate the combined bacteria. mixing the medium in the step (2) with the first generation of combined yeast and lactic acid bacteria in the step (7) according to the weight ratio of 1:1, and spraying sterile water until moistened to wet and scattered, with water dripping out when hold by hand; then placing it in sterile condition with the temperature above 26° C. for more than 48 hours of aerobic activation, until the surface of the medium appears white or milky white bacterial plaque evenly distributed, and there is a wet and sticky feeling and light fermentation fragrance when pushing the surface aside; then providing the mixed medium into the closed environment for continued fermentation, until the gradual depletion of surrounding oxygen and entering into anaerobic fermentation; the combined bacteria domestication can be regarded as finished when processing anaerobic fermentation for 20-30 days until the colony yeast and lactic acid bacteria combination grows vigorously;

(9) Packaging of the combined bacteria: the domesticated yeast and lactic acid bacteria combination in the step (8) are vacuum packed according to 5-10 kg/bag, isolation of air to eliminate aerobic bacteria infection and thoroughly eliminate the possible residual by the first generation of strains of *Aspergillus, Mucor* and other fungal spores, thus allowing easy industrial transport and application.

This embodiment tested the yeast and lactic acid bacteria combination after packaging in step (9), the average value of viable yeast is more than 6.4×10$^4$ cfu/ml, the average value of viable lactic acid bacteria is more than 4×10$^8$ cfu/ml, the value of the mould in harmful bacteria is <10 cfu/ml; *Escherichia coli* <30 cfu/ml; *Salmonella* ND; *Shigella* ND. *Staphylococcus aureus* ND (ND means not detected).

Embodiment 2

A yeast and lactic acid bacteria combination, the cultivation method comprises the following steps:

(1) Inoculum extraction: taking the pit mud fermentation from the Chinese liquor brewing mud pit form the different orientation, and the different directions mentioned refer to the east, south, west and north, the pit walls and the bottom of the pit; adding sterile water with the temperature of 35-38° C. to the pit mud fermentation in accordance with the weight ratio of 2:1, and letting stand for use after mixing sufficiently; the brewing pit in this embodiment is a traditional brewing pit of Chinese liquor in the Yaowan ancient town in northern Jiangsu Province;

(2) Culture medium preparation: taking 4 parts of sorghum rice, 3 parts of mashed potato powder, 1 part of wheat germ and 1 part of glutinous rice as the main ingredients for preparation; taking raw materials in accordance with the weight ratio of 1:1 and adding water and stirring sufficiently; and after steam distillation for 40 minutes until the granular swelling, the culture medium can be placed in a sterile container for heat dissipation; and cooling the temperature of medium to below 45° C. for use;

(3) Strain inoculation: the pit mud fermentation in the step (1) and the prepared medium in the step (2) are mixed evenly according to the weight ratio of 1:2, and then placed in an aseptic conditions with the temperature above 26° C. for constant temperature aerobic cultivation for over 45 hours and it is necessary to pay attention to the medium changes during this process;

(4) Anaerobic breeding: when the medium in the step (3) appears white or milky white bacterial plaque evenly distributed, and there is a wet and sticky feeling and light fermentation fragrance when pushing the surface aside; the medium will be packed in separate bags according to 1-5 kg respectively and the medium will continue to ferment at a constant temperature of 37° C. after being packed in separate bags;

In this step, due to the previous culture with a large number of aerobic colonies, there will be the output of gas after sealing the bag, therefore, it is necessary to pay attention to the appropriate time to release the gas and reduce the pressure.

(5) Obtain facultative anaerobes yeast and lactic acid bacteria combination: after depleting the residual oxygen in the bag, the medium in the bag appears agglomeration in vacuum with white, creamy white bacterial plaque and covered with bacterial film. When covered by the bacterial film, a variety of aerobic bacteria of *Aspergillus* and *Mucor* species will enter into apoptosis, the main survival with slow proliferation is facultative anaerobe yeast and lactic acid bacteria combination;

(6) Facultative anaerobes yeast and lactic acid bacteria combination optimization: the medium packed in the bag in the step (5) will continue anaerobic fermentation to allow facultative anaerobes bacteria to continue to proliferate and further exclude aerobic bacteria, until the white, milky white bacterial film completely covers the medium, to complete occupancy and saturated fermentation; the aerobic bacteria have almost no survival conditions at this time (there may exist a very few fungal spores but they will be completely eliminated due to the suppression of community dominance and subsequent processes); at the same time, the facultative anaerobe bacteria are gradually entering a dormant state and waiting for recovery;

(7) Sampling and testing to identify the obtained symbiotic colonies: testing the activity of the combined bacteria in the step (6), and when the average value of viable yeast is 6.4×10$^4$ cfu/ml or more; the average value of viable lactic acid bacteria is $4\times10^8$ cfu/ml or more, the first generation of yeast and lactic acid bacteria combination is obtained;

In this embodiment, the maximum value of viable yeast is $3.1\times10^5$ cfu/ml and the maximum value of viable lactic acid bacteria is $1.2\times10^9$ cfu/ml.

(8) Combined bacteria domestication: due to the acquisition of the combined colonies, out of the complementary of the large communities of *Aspergillus* and *Mucor*, forming symbiotic adaptations between new small communities, adaptations to the medium and adaptations to changes in the survival environment such as the conversion of aerobic and anaerobic environments, therefore it is necessary to domesticate the combined bacteria. mixing the medium in the step (2) with the first generation of combined yeast and lactic acid bacteria in the step (7) according to the weight ratio of 1:1, and spraying sterile water until moistened to wet and scattered, with water dripping out when hold by hand; then placing it in sterile condition with the temperature above 26° C. for more than 48 hours of aerobic activation, until the surface of the medium appears white or milky white bacterial plaque evenly distributed, and there is a wet and sticky feeling and light fermentation fragrance when pushing the surface aside; then providing the mixed medium into the closed environment for continued fermentation, until the gradual depletion of surrounding oxygen and entering into anaerobic fermentation; the combined bacteria domestication can be regarded as finished when processing anaerobic fermentation for 20-30 days until the colony yeast and lactic acid bacteria combination grows vigorously;

(9) Packaging of the combined bacteria: the domesticated yeast and lactic acid bacteria combination in the step (8) are vacuum packed according to 5-10 kg/bag, isolation of air to eliminate aerobic bacteria infection and thoroughly eliminate the possible residual by the first generation of strains of *Aspergillus, Mucor* and other fungal spores, thus allowing easy industrial transport and application.

This embodiment tested the yeast and lactic acid bacteria combination after packaging in step (9), the average value of viable yeast is more than $6.4\times10^4$ cfu/ml, the average value of viable lactic acid bacteria is more than $4\times10^8$ cfu/ml, the value of the mould in harmful bacteria is <10 cfu/ml; *Escherichia coli* <30 cfu/ml; *Salmonella* ND; *Shigella* ND. *Staphylococcus aureus* ND (ND means not detected).

Embodiment 3

A yeast and lactic acid bacteria combination, the cultivation method comprises the following steps:

(1) Inoculum extraction: taking the pit mud fermentation from the Chinese liquor brewing mud pit form the different orientation, and the different directions mentioned refer to the east, south, west and north, the pit walls and the bottom of the pit; adding sterile water with the temperature of 35-38° C. to the pit mud fermentation in accordance with the weight ratio of 2:1, and letting stand for use after mixing sufficiently; the brewing pit in this embodiment is a traditional brewing pit of Chinese liquor in the Yaowan ancient town in northern Jiangsu Province;

(2) Culture medium preparation: taking 3.8 parts of sorghum rice, 3 parts of mashed potato powder, 0.95 parts of wheat germ, 1 part of buckwheat, 1 part of glutinous rice, 0.25 parts of HFCS (high fructose corn syrup) as the main ingredients for preparation; taking raw materials in accordance with the weight ratio of 1:1 and adding water and stirring sufficiently; and after steam distillation for 40 minutes until the granular swelling, the culture medium can be placed in a sterile container for heat dissipation; and cooling the temperature of medium to below 45° C. for use;

(3) Strain inoculation: the pit mud fermentation in the step (1) and the prepared medium in the step (2) are mixed evenly according to the weight ratio of 1:2, and then placed in an aseptic conditions with the temperature above 26° C. for constant temperature aerobic cultivation for over 45 hours and it is necessary to pay attention to the medium changes during this process;

(4) Anaerobic breeding: when the medium in the step (3) appears white or milky white bacterial plaque evenly distributed, and there is a wet and sticky feeling and light fermentation fragrance when pushing the surface aside; the medium will be packed in separate bags according to 1-5 kg respectively and the medium will continue to ferment at a constant temperature of 37° C. after being packed in separate bags;

In this step, due to the previous culture with a large number of aerobic colonies, there will be the output of gas after sealing the bag, therefore, it is necessary to pay attention to the appropriate time to release the gas and reduce the pressure.

(5) Obtain facultative anaerobes combined bacteria of yeast and lactic acid bacteria combination: after depleting the residual oxygen in the bag, the medium in the bag appears agglomeration in vacuum with white, creamy white bacterial plaque and covered with bacterial film. When covered by the bacterial film, a variety of aerobic bacteria of *Aspergillus* and *Mucor* species will enter into apoptosis, the main survival with slow proliferation is facultative anaerobe yeast and lactic acid bacteria combination;

(6) Facultative anaerobes yeast and lactic acid bacteria combination optimization: the medium packed in the bag in the step (5) will continue anaerobic fermentation to allow facultative anaerobes bacteria to continue to proliferate and further exclude aerobic bacteria, until the white, milky white bacterial film completely covers the medium, to complete occupancy and saturated fermentation; the aerobic bacteria have almost no survival conditions at this time (there may exist a very few fungal spores but they will be completely eliminated due to the suppression of community dominance and subsequent processes); at the same time, the facultative anaerobe bacteria are gradually entering a dormant state and waiting for recovery;

(7) Sampling and testing to identify the obtained symbiotic colonies: testing the activity of the combined bacteria in the step (6), and when the average value of viable yeast is $6.4\times10^4$ cfu/ml or more; the average value of viable lactic acid bacteria is $4\times10^8$ cfu/ml or more, the first generation of yeast and lactic acid bacteria combination is obtained;

In this embodiment, the maximum value of viable yeast is $3.1\times10^5$ cfu/ml and the maximum value of viable lactic acid bacteria is $1.2\times10^9$ cfu/ml.

(8) Combined bacteria domestication: due to the acquisition of the combined colonies, out of the complementary of the large communities of *Aspergillus* and *Mucor*, forming symbiotic adaptations between new small communities, adaptations to the medium and adaptations to changes in the survival environment such as the conversion of aerobic and anaerobic environments, therefore it is necessary to domesticate the combined bacteria. mixing the medium in the step (2) with the first generation of yeast and lactic acid bacteria combination in the step (7) according to the weight ratio of 1:1, and spraying sterile water until moistened to wet and scattered, with water dripping out when hold by hand; then placing it in sterile condition with the temperature above 26° C. for more than 48 hours of aerobic activation, until the surface of the medium appears white or milky white bacterial plaque evenly distributed, and there is a wet and sticky feeling and light fermentation fragrance when pushing the surface aside; then providing the mixed medium into the closed environment for continued fermentation, until the gradual depletion of surrounding oxygen and entering into anaerobic fermentation; the combined bacteria domestication can be regarded as finished when processing anaerobic fermentation for 20-30 days until the colony yeast and lactic acid bacteria combination grows vigorously;

(9) Packaging of the combined bacteria: the domesticated yeast and lactic acid bacteria combination in the step (8) are vacuum packed according to 5-10 kg/bag, isolation of air to eliminate aerobic bacteria infection and thoroughly eliminate the possible residual by the first generation of strains of *Aspergillus, Mucor* and other fungal spores, thus allowing easy industrial transport and application.

This embodiment tested the yeast and lactic acid bacteria combination after packaging in step (9), the average value of viable yeast is more than $6.4 \times 10^4$ cfu/ml, the average value of viable lactic acid bacteria is more than $4 \times 10^8$ cfu/ml, the value of the mould in harmful bacteria is <10 cfu/ml; *Escherichia coli* <30 cfu/ml; *Salmonella* ND; *Shigella* ND. *Staphylococcus aureus* ND (ND means not detected).

The combined bacteria in step (9) of embodiments 1 to 3 were separated and purified according to the conventional method to obtain six species of bacteria, which are *Candida ethanolica, Lentilactobacillus buchneri, Lactobacillus paracasei, Lactobacillus zeae, Lactobacillus plantarum* and *Lactobacillus chiayiensis* respectively. In the invention, it is named as *Candida ethanolica* B-JJ1, *Lentilactobacillus buchneri* B-JR1, *Lactobacillus paracasei* B-JR2, *Lactobacillus zeae* B-JR4, *Lactobacillus plantarum* B-JR5 and *Lactobacillus chiayiensis* B-JR6 respectively. Each fermentation strain was separated and purified for testing, and the colony and cell morphology of each strain are shown in FIG. 1 to FIG. 7 respectively, and the physicochemical and biochemical identification of each strain was carried out, and the results are shown in Tables 1 to 12 respectively.

TABLE 1

| Physiological and Biochemical Characteristics of *Candida Ethanolica* B-JJ1 | | |
| --- | --- | --- |
| | Testing Items | Results |
| A1 | Negative Control | – |
| A2 | Dextrin | – |
| A3 | D-Maltose | – |
| A4 | D-Trehalose | – |
| A5 | D-Cellobiose | – |
| A6 | Gentiobiose | – |
| A7 | Sucrose | – |
| A8 | D-Turanose | – |
| A9 | Stachyose | – |

TABLE 1-continued

| Physiological and Biochemical Characteristics of *Candida Ethanolica* B-JJ1 | | |
| --- | --- | --- |
| | Testing Items | Results |
| A10 | Positive Control | – |
| A11 | Ph6 | – |
| A12 | Ph5 | + |
| B1 | Raffinose | – |
| B2 | A-D-Lactose | – |
| B3 | Melibiose | – |
| B4 | B-Formyl-D-Glucoside | – |
| B5 | D-Salicin | – |
| B6 | N-Acetyl-D-Glucosamine | – |
| B7 | N-Acetyl-B-D-Mannosamine | – |
| B8 | N-Acetyl-D-Galactosamine | – |
| B9 | N-Acetylneuraminic Acid | – |
| B10 | 1% Nacl | – |
| B11 | 4% Nacl | – |
| B12 | 8% Nacl | – |
| C1 | A-D-Glucose | – |
| C2 | D-Mannose | W |
| C3 | D-Fructose | – |
| C4 | D-Galactose | – |
| C5 | 3-Formyl Glucose | – |
| C6 | D-Fucose | – |
| C7 | L-Fucose | – |
| C8 | L-Rhamnose | – |
| C9 | Inosine | – |
| C10 | Sodium Lactate | – |
| C11 | Fusidic Acid | – |
| C12 | D-Serine | – |
| D1 | D-Sorbitol | – |
| D2 | D-Mannitol | – |
| D3 | D-Arabinol | + |
| D4 | Inositol | + |
| D5 | Glycerol | + |
| D6 | D-Glucose-6-Phosphoric Acid | – |
| D7 | D-Fructose-6-Phosphoric Acid | – |
| D8 | D-Aspartic Acid | – |
| D9 | D-Serine | – |
| D10 | Troleandomycin | – |
| D11 | Rifamycin SV | – |
| D12 | Minocycline | + |
| E1 | Gelatin | – |
| E2 | E-Aminoacetyl-L-Proline | – |
| E3 | L-Alanine | – |
| E4 | L-Arginine | – |
| E5 | L-Aspartic Acid | – |
| E6 | L-Glutamic Acid | – |
| E7 | L-Histamine | – |
| E8 | L-Pyroglutamic Acid | – |
| E9 | L-Serine | – |
| E10 | Clindamycin | – |
| E11 | Guanidinium Chloride | – |
| E12 | Tetradecyl Sodium Sulfate | – |
| F1 | Pectin | + |
| F2 | D-Galacturonic Acid | – |
| F3 | L-Galactonolactone | + |
| F4 | D-Gluconic Acid | – |
| F5 | D-Glucuronic Acid | – |
| F6 | Glucuronamide | – |
| F7 | Muconic Acid | – |
| F8 | Quinic Acid | – |
| F9 | Saccharic Acid | – |
| F10 | Vancomycin | + |
| F11 | Tetrazolium Violet | – |
| F12 | Tetrazolium Blue | – |
| G1 | P-Hydroxy-Phenylacetic Acid | – |
| G2 | Methyl Pyruvate | – |
| G3 | D-Methyl Lactate | – |
| G4 | L-Lactic Acid | – |
| G5 | Citric Acid | – |
| G6 | A-Ketoglutaric Acid | – |
| G7 | D-Malic Acid | – |
| G8 | L-Malic Acid | – |
| G9 | Bromosuccinic Acid | – |
| G10 | Nalidixic Acid | – |
| G11 | Lithium Chloride | – |
| G12 | Potassium Tellurite | – |

TABLE 1-continued

Physiological and Biochemical
Characteristics of *Candida Ethanolica* B-JJ1

| | Testing Items | Results |
|---|---|---|
| H1 | Tween 40 | − |
| H2 | Γ-Amio-Butyric Acid | + |
| H3 | A-Hydroxy-Butyrate | − |
| H4 | B-Hydroxy-D,L-Butyrate | − |
| H5 | A-Ketobutyric Acid | − |
| H6 | Acetoacetic Acid | − |
| H7 | Propionic Acid | − |
| H8 | Acetic Acid | − |
| H9 | Formic Acid | − |
| H10 | Aztreonam | − |
| H11 | Sodium Butyrate | − |
| H12 | Sodium Bromate | − |

Note:
'+' is positive, '−' is negative.

TABLE 2

Physiological and Biochemical Characteristics of
*Lentilactobacillus Buchneri* B-JR1-Enzyme Activity

| No. | | Tested Enzyme/Substrate | Result |
|---|---|---|---|
| 1 | Water | | − |
| 2 | Alkaline Phosphatase | 2-Naphthyl Phosphate | − |
| 3 | Esterase (C4) | 2-Naphthyl Butyrate | + |
| 4 | Lipid Esterase(C8) | 2-Naphthyl Octanoate | + |
| 5 | Lipoid(C14) | 2-Naphthyl Myristate | − |
| 6 | Leucine Aromatic Amine | L-Leucyl-2-Naphthylamine | + |
| 7 | Valine Aromatic Amine | L-Valinyl-2-Naphthylamine | + |
| 8 | Cystine Aromatic Amine | L-Cystinyl-2-Naphthylamine | − |
| 9 | Trypsin | N-Benzoyl-DL-Argininyl-2-Naphthylamine | − |
| 10 | Chymotrypsin | N-Glutaryl-Phenylalanine-2-Naphthylamine | − |
| 11 | Acid Phosphatase | N-Naphthyl-Phosphate | + |
| 12 | Naphthol-AS-BI-Phosphatase | Naphthol-AS-BI-Phosphate | + |
| 13 | A-Galactosidase | 6-Bromo-2-Naphthyl-AD-GALACTOPYRANOSIDE | − |
| 14 | B-Galactosidase | 2-Naphthyl-BD-Galactopyranoside | + |
| 15 | B-Alduronic Acid Glucosidase | Naphthol-AS-BD-Glucuronide | + |
| 16 | A-Glucosidases | 2-Naphthyl-AD-Glucopyranoside | − |
| 17 | B-Glucosidases | 6-Bromo-2-Naphthyl-BD-Glucopyranoside | − |
| 18 | N-Acetyl-Glucosaminidase | 1-Naphthyl-N-Acetyl-BD-Glucosamine | − |
| 19 | A-Mannosidase | 6-Bromo-2-Naphthyl-AD-Pyran-Mannoside | − |
| 20 | B-Glucosidase | 2-Naphthyl-AL-Fructopyranoside | − |

TABLE 3

Physiological and Biochemical Properties of *Lentilactobacillus
Buchneri* B-JR1-Acid Production Using Carbon Source

| Corresponding Tubes/ Substrates For Reagent Strips | Result |
|---|---|
| 0 Control | − |
| 1 Glycerol | − |
| 2 Erythritol | − |
| 3 D-Arabinose | − |
| 4 L-Arabinose | + |
| 5 Ribose | + |
| 6 D-Xylose | + |
| 7 L-Xylose | − |

TABLE 3-continued

Physiological and Biochemical Properties of *Lentilactobacillus
Buchneri* B-JR1-Acid Production Using Carbon Source

| Corresponding Tubes/ Substrates For Reagent Strips | Result |
|---|---|
| 8 Adonol | − |
| 9 B-Methyl-D-Glucoside | − |
| 10 Galactose | + |
| 11 Glucose | − |
| 12 Fructose | + |
| 13 Mannose | − |
| 14 Sorbitose | − |
| 15 Rhamnose | − |
| 16 Dulcitol | − |
| 17 Inositol | − |
| 18 Mannitol | − |
| 19 Sorbitol | − |
| 20 A-Methyl-D-Mannoside | − |
| 21 A-Methyl-D-Glucoside | − |
| 22 N-Acetyl-Glucosamine | − |
| 23 Amygdalin | − |
| 24 Arbutin | − |
| 25 Esculin | + |
| 26 Salicin | − |
| 27 Cellobiose | − |
| 28 Maltose | − |
| 29 Lactose | + |
| 30 Melibiose | W |
| 31 Sucrose | W |
| 32 Trehalose | − |
| 33 Inulin | − |
| 34 Melezitose | − |
| 35 Raffinose | W |
| 36 Starch | − |
| 37 Glycogen | − |
| 38 Xylitol | − |
| 39 Geraniol | − |
| 40 D-Turanose | − |
| 41 D-Lysose | − |
| 42 D-Tagatose | − |
| 43 D-Fucose | − |
| 44 L-Fucose | − |
| 45 D-Arabinitol | − |
| 46 L-Arabinitol | − |
| 47 Gluconate | − |
| 48 2-Keto-Gluconate | − |
| 49 5-Keto-Gluconate | − |

Note:
'+' is positive, '−' is negative, and 'W' is a weakly positive reaction.

TABLE 4

Physiological and Biochemical Properties of *Lactobacillus
Paracasei* B-JR2—Enzyme Activity & Carbon Source Oxidation

| | | Reaction Substrates/ Reaction Enzymes | Result |
|---|---|---|---|
| ONPG | Nitrophenyl-Galactopyranoside | B-Galactosidase | − |
| ADH | Arginine | Arginine Dihydrolase | − |
| LDC | Lysine | Lysine Decarboxylase | − |
| ODC | Ornithine | Ornithine Decarboxylase | − |
| CIT | Trisodium Citrate | Citrate Utilization | − |
| H2S | Sodium Thiosulfate | H2S Production | − |
| URE | Urea | Urease | − |
| TDA | Tryptophan | Tryptophan Deaminase | − |
| IND | Tryptophan | Indole Production | − |
| VP | Pyruvate | 3-Hydroxybutanone Producing Acetylmethylcarbinol | + |
| GEL | Kohn Gelatin | Gelatinase | − |
| GLU | Glucose | Fermentation/Oxidation (4) | + |
| MAN | Mannitol | Fermentation/Oxidation (4) | − |
| INO | Inositol | Fermentation/Oxidation (4) | − |
| SOR | Sorbitol | Fermentation/Oxidation (4) | − |
| RHA | Rhamnose | Fermentation/Oxidation (4) | − |

TABLE 4-continued

Physiological and Biochemical Properties of *Lactobacillus Paracasei* B-JR2—Enzyme Activity & Carbon Source Oxidation

| | | Reaction Substrates/ Reaction Enzymes | Result |
|---|---|---|---|
| SAC | Sucrose | Fermentation/Oxidation (4) | – |
| MEL | Melibiose | Fermentation/Oxidation (4) | – |
| AMY | Amygdalin | Fermentation/Oxidation (4) | – |
| ARA | Arabinose | Fermentation/Oxidation (4) | – |

TABLE 5

Physiological and Biochemical Properties of *Lactobacillus Paracasei* B-JR2—Acid Production Using Carbon Source

| Corresponding Tubes/ Substrates For Reagent Strips | Result |
|---|---|
| 0 Control | – |
| 1 Glycerol | – |
| 2 Erythritol | – |
| 3 D-Arabinose | – |
| 4 L-Arabinose | – |
| 5 Ribose | + |
| 6 D-Xylose | – |
| 7 L-Xylose | – |
| 8 Adonol | – |
| 9 B-Methyl-D-Glucoside | – |
| 10 Galactose | + |
| 11 Glucose | + |
| 12 Fructose | + |
| 13 Mannose | + |
| 14 Sorbitose | – |
| 15 Rhamnose | – |
| 16 Dulcitol | + |
| 17 Inositol | – |
| 18 Mannitol | + |
| 19 Sorbitol | + |
| 20 A-Methyl-D-Mannoside | – |
| 21 A-Methyl-D-Glucoside | + |
| 22 N-Acetyl-Glucosamine | + |
| 23 Amygdalin | + |
| 24 Arbutin | + |
| 25 Esculin | + |
| 26 Salicin | – |
| 27 Cellobiose | + |
| 28 Maltose | + |
| 29 Lactose | – |
| 30 Melibiose | – |
| 31 Sucrose | + |
| 32 Trehalose | + |
| 33 Inulin | – |
| 34 Melezitose | + |
| 35 Raffinose | – |
| 36 Starch | – |
| 37 Glycogen | – |
| 38 Xylitol | – |
| 39 Geraniol | – |
| 40 D-Turanose | + |
| 41 D-Lysose | – |
| 42 D-Tagatose | + |
| 43 D-Fucose | – |
| 44 L-Fucose | – |
| 45 D-Arabinitol | – |
| 46 L-Arabinitol | – |
| 47 Gluconate | – |
| 48 2-Keto-Gluconate | – |
| 49 5-Keto-Gluconate | – |

TABLE 6

Physiological and Biochemical Characteristics of *Lactobacillus Zeae* B-JR4—Enzyme Activity

| No. | | Tested Enzyme/Substrate | Result |
|---|---|---|---|
| 1 | Water | | – |
| 2 | Alkaline Phosphatase | 2-Naphthyl Phosphate | – |
| 3 | Esterase (C4) | 2-Naphthyl Butyrate | + |
| 4 | Lipid Esterase(C8) | 2-Naphthyl Octanoate | + |
| 5 | Lipoid(C14) | 2-Naphthyl Myristate | – |
| 6 | Leucine Aromatic Amine | L-Leucyl-2-Naphthylamine | + |
| 7 | Valine Aromatic Amine | L-Valinyl-2-Naphthylamine | + |
| 8 | Cystine Aromatic Amine | L-Cystinyl-2-Naphthylamine | – |
| 9 | Trypsin | N-Benzoyl-DL-Argininyl-2-Naphthylamine | – |
| 10 | Chymotrypsin | N-Glutaryl-Phenylalanine-2-Naphthylamine | – |
| 11 | Acid Phosphatase | N-Naphthyl-Phosphate | + |
| 12 | Naphthol-AS-BI-Phosphatase | Naphthol-AS-BI-Phosphate | + |
| 13 | A-Galactosidase | 6-Bromo-2-Naphthyl-AD-GALACTOPYRANOSIDE | – |
| 14 | B-Galactosidase | 2-Naphthyl-BD-Galactopyranoside | + |
| 15 | B-Alduronic Acid Glucosidase | Naphthol-AS-BD-Glucuronide | + |
| 16 | A-Glucosidases | 2-Naphthyl-AD-Glucopyranoside | – |
| 17 | B-Glucosidases | 6-Bromo-2-Naphthyl-BD-Glucopyranoside | – |
| 18 | N-Acetyl-Glucosaminidase | 1-Naphthyl-N-Acetyl-BD-Glucosamine | – |
| 19 | A-Mannosidase | 6-Bromo-2-Naphthyl-AD-Pyran-Mannoside | – |
| 20 | B-Glucosidase | 2-Naphthyl-AL-Fructopyranoside | – |

TABLE 7

Physiological and Biochemical Properties of *Lactobacillus Zeae* B-JR4—Acid Production Using Carbon Source

| Corresponding Tubes/ Substrates For Reagent Strips | Result |
|---|---|
| 0 Control | – |
| 1 Glycerol | + |
| 2 Erythritol | – |
| 3 D-Arabinose | + |
| 4 L-Arabinose | + |
| 5 Ribose | + |
| 6 D-Xylose | + |
| 7 L-Xylose | – |
| 8 Adonol | + |
| 9 B-Methyl-D-Glucoside | – |
| 10 Galactose | + |
| 11 Glucose | + |
| 12 Fructose | + |
| 13 Mannose | + |
| 14 Sorbitose | – |
| 15 Rhamnose | – |
| 16 Dulcitol | + |
| 17 Inositol | W |
| 18 Mannitol | + |
| 19 Sorbitol | + |
| 20 A-Methyl-D-Mannoside | – |
| 21 A-Methyl-D-Glucoside | – |
| 22 N-Acetyl-Glucosamine | – |
| 23 Amygdalin | + |
| 24 Arbutin | + |
| 25 Esculin | + |
| 26 Salicin | + |
| 27 Cellobiose | + |
| 28 Maltose | + |
| 29 Lactose | + |
| 30 Melibiose | + |
| 31 Sucrose | + |

TABLE 7-continued

Physiological and Biochemical Properties of *Lactobacillus Zeae* B-JR4—Acid Production Using Carbon Source

| Corresponding Tubes/ Substrates For Reagent Strips | Result |
|---|---|
| 32 Trehalose | + |
| 33 Inulin | − |
| 34 Melezitose | + |
| 35 Raffinose | + |
| 36 Starch | − |
| 37 Glycogen | − |
| 38 Xylitol | − |
| 39 Geraniol | − |
| 40 D-Turanose | + |
| 41 D-Lysose | − |
| 42 D-Tagatose | + |
| 43 D-Fucose | − |
| 44 L-Fucose | + |
| 45 D-Arabinitol | + |
| 46 L-Arabinitol | + |
| 47 Gluconate | − |
| 48 2-Keto-Gluconate | − |
| 49 5-Keto-Gluconate | − |

TABLE 8

Physiological and Biochemical Properties of *Lactobacillus Plantarum* B-JR5—Enzyme Activity, Carbon Source Oxidation

| | Reaction Substrates/ | Reaction Enzymes | Result |
|---|---|---|---|
| ONPG | Nitrophenyl-Galactopyranoside | B-Galactosidase | − |
| ADH | Arginine | Arginine Dihydrolase | − |
| LDC | Lysine | Lysine Decarboxylase | − |
| ODC | Ornithine | Ornithine Decarboxylase | − |
| CIT | Trisodium Citrate | Citrate Utilization | − |
| H2S | Sodium Thiosulfate | H2S Production | − |
| URE | Urea | Urease | − |
| TDA | Tryptophan | Tryptophan Deaminase | − |
| IND | Tryptophan | Indole Production | − |
| VP | Pyruvate | 3-Hydroxybutanone Producing Acetylmethylcarbinol | + |
| GEL | Kohn Gelatin | Gelatinase | − |
| GLU | Glucose | Fermentation/Oxidation (4) | + |
| MAN | Mannitol | Fermentation/Oxidation (4) | W |
| INO | Inositol | Fermentation/Oxidation (4) | − |
| SOR | Sorbitol | Fermentation/Oxidation (4) | − |
| RHA | Rhamnose | Fermentation/Oxidation (4) | − |
| SAC | Sucrose | Fermentation/Oxidation (4) | − |
| MEL | Melibiose | Fermentation/Oxidation (4) | − |
| AMY | Amygdalin | Fermentation/Oxidation (4) | W |
| ARA | Arabinose | Fermentation/Oxidation (4) | − |

TABLE 9

Physiological and Biochemical Properties of *Lactobacillus Plantarum* B-JR5-Acid Production Using Carbon Source

| Corresponding Tubes/ Substrates For Reagent Strips | Result |
|---|---|
| 0 Control | − |
| 1 Glycerol | − |
| 2 Erythritol | − |
| 3 D-Arabinose | − |
| 4 L-Arabinose | + |
| 5 Ribose | + |
| 6 D-Xylose | − |
| 7 L-Xylose | − |
| 8 Adonol | − |
| 9 B-Methyl-D-Glucoside | − |
| 10 Galactose | + |

TABLE 9-continued

Physiological and Biochemical Properties of *Lactobacillus Plantarum* B-JR5-Acid Production Using Carbon Source

| Corresponding Tubes/ Substrates For Reagent Strips | Result |
|---|---|
| 11 Glucose | + |
| 12 Fructose | + |
| 13 Mannose | + |
| 14 Sorbitose | − |
| 15 Rhamnose | − |
| 16 Dulcitol | − |
| 17 Inositol | − |
| 18 Mannitol | + |
| 19 Sorbitol | + |
| 20 A-Methyl-D-Mannoside | + |
| 21 A-Methyl-D-Glucoside | − |
| 22 N-Acetyl-Glucosamine | + |
| 23 Amygdalin | + |
| 24 Arbutin | + |
| 25 Esculin | + |
| 26 Salicin | + |
| 27 Cellobiose | + |
| 28 Maltose | + |
| 29 Lactose | + |
| 30 Melibiose | − |
| 31 Sucrose | + |
| 32 Trehalose | + |
| 33 Inulin | − |
| 34 Melezitose | + |
| 35 Raffinose | − |
| 36 Starch | − |
| 37 Glycogen | − |
| 38 Xylitol | − |
| 39 Geraniol | + |
| 40 D-Turanose | + |
| 41 D-Lysose | − |
| 42 D-Tagatose | − |
| 43 D-Fucose | − |
| 44 L-Fucose | − |
| 45 D-Arabinitol | − |
| 46 L-Arabinitol | − |
| 47 Gluconate | − |
| 48 2-Keto-Gluconate | − |
| 49 5-Keto-Gluconate | − |

TABLE 10

Physiological and Biochemical Properties of *Lactobacillus Plantarum* B-JR5—Acid Production Using Carbon Source

| Corresponding Tubes/ Substrates For Reagent Strips | Result |
|---|---|
| 0 Control | − |
| 1 Glycerol | − |
| 2 Erythritol | − |
| 3 D-Arabinose | − |
| 4 L-Arabinose | + |
| 5 Ribose | + |
| 6 D-Xylose | − |
| 7 L-Xylose | − |
| 8 Adonol | − |
| 9 B-Methyl-D-Glucoside | − |
| 10 Galactose | + |
| 11 Glucose | + |
| 12 Fructose | + |
| 13 Mannose | + |
| 14 Sorbitose | − |
| 15 Rhamnose | − |
| 16 Dulcitol | − |
| 17 Inositol | − |
| 18 Mannitol | + |
| 19 Sorbitol | + |
| 20 A-Methyl-D-Mannoside | + |
| 21 A-Methyl-D-Glucoside | − |
| 22 N-Acetyl-Glucosamine | + |

TABLE 10-continued

Physiological and Biochemical Properties of *Lactobacillus Plantarum* B-JR5—Acid Production Using Carbon Source

| Corresponding Tubes/ Substrates For Reagent Strips | Result |
|---|---|
| 23 Amygdalin | + |
| 24 Arbutin | + |
| 25 Esculin | + |
| 26 Salicin | + |
| 27 Cellobiose | + |
| 28 Maltose | + |
| 29 Lactose | + |
| 30 Melibiose | − |
| 31 Sucrose | + |
| 32 Trehalose | + |
| 33 Inulin | − |
| 34 Melezitose | + |
| 35 Raffinose | − |
| 36 Starch | − |
| 37 Glycogen | − |
| 38 Xylitol | − |
| 39 Geraniol | + |
| 40 D-Turanose | + |
| 41 D-Lysose | − |
| 42 D-Tagatose | − |
| 43 D-Fucose | − |
| 44 L-Fucose | − |
| 45 D-Arabinitol | − |
| 46 L-Arabinitol | − |
| 47 Gluconate | − |
| 48 2-Keto-Gluconate | − |
| 49 5-Keto-Gluconate | − |

TABLE 11

Physiological and Biochemical Characteristics of *Lactobacillus Chiayiensis* B-JR6—Enzyme Activity

| No. | | Tested Enzyme/Substrate | Result |
|---|---|---|---|
| 1 | Water | | − |
| 2 | Alkaline Phosphatase | 2-Naphthyl Phosphate | + |
| 3 | Esterase (C4) | 2-Naphthyl Butyrate | + |
| 4 | Lipid Esterase(C8) | 2-Naphthyl Octanoate | + |
| 5 | Lipoid(C14) | 2-Naphthyl Myristate | + |
| 6 | Leucine Aromatic Amine | L-Leucyl-2-Naphthylamine | + |
| 7 | Valine Aromatic Amine | L-Valinyl-2-Naphthylamine | + |
| 8 | Cystine Aromatic Amine | L-Cystinyl-2-Naphthylamine | + |
| 9 | Trypsin | N-Benzoyl-DL-Argininyl-2-Naphthylamine | + |
| 10 | Chymotrypsin | N-Glutaryl-Phenylalanine 2-Naphthylamine | + |
| 11 | Acid Phosphatase | N-Naphthyl-Phosphate | + |
| 12 | Naphthol-AS-BI-Phosphatase | Naphthol-AS-BI-Phosphate | + |
| 13 | A-Galactosidase | 6-Bromo-2-Naphthyl-AD-GALACTOPYRANOSIDE | − |
| 14 | B-Galactosidase | 2-Naphthyl-BD-Galactopyranoside | + |
| 15 | B-Alduronic Acid Glucosidase | Naphthol-AS-BD-Glucuronide | + |
| 16 | A-Glucosidases | 2-Naphthyl-AD-Glucopyranoside | + |
| 17 | B-Glucosidases | 6-Bromo-2-Naphthyl-BD-Glucopyranoside | + |
| 18 | N-Acetyl-Glucosaminidase | 1-Naphthyl-N-Acetyl-BD-Glucosamine | W |
| 19 | A-Mannosidase | 6-Bromo-2-Naphthyl-AD-Pyran-Mannoside | − |
| 20 | B-Glucosidase | 2-Naphthyl-AL-Fructopyranoside | − |

TABLE 12

Physiological and Biochemical Properties of *Lactobacillus Chiayiensis* B-JR6—Acid Production Using Carbon Source

| Corresponding Tubes/ Substrates For Reagent Strips | Result |
|---|---|
| 0 Control | − |
| 1 Glycerol | − |
| 2 Erythritol | − |
| 3 D-Arabinose | + |
| 4 L-Arabinose | + |
| 5 Ribose | + |
| 6 D-Xylose | − |
| 7 L-Xylose | − |
| 8 Adonol | + |
| 9 B-Methyl-D-Glucoside | − |
| 10 Galactose | + |
| 11 Glucose | + |
| 12 Fructose | + |
| 13 Mannose | + |
| 14 Sorbitose | − |
| 15 Rhamnose | + |
| 16 Dulcitol | − |
| 17 Inositol | − |
| 18 Mannitol | + |
| 19 Sorbitol | + |
| 20 A-Methyl-D-Mannoside | + |
| 21 A-Methyl-D-Glucoside | − |
| 22 N-Acetyl-Glucosamine | + |
| 23 Amygdalin | + |
| 24 Arbutin | − |
| 25 Esculin | + |
| 26 Salicin | + |
| 27 Cellobiose | + |
| 28 Maltose | − |
| 29 Lactose | + |
| 30 Melibiose | − |
| 31 Sucrose | + |
| 32 Trehalose | + |
| 33 Inulin | − |
| 34 Melezitose | − |
| 35 Raffinose | − |
| 36 Starch | − |
| 37 Glycogen | − |
| 38 Xylitol | − |
| 39 Geraniol | + |
| 40 D-Turanose | + |
| 41 D-Lysose | − |
| 42 D-Tagatose | + |
| 43 D-Fucose | − |
| 44 L-Fucose | + |
| 45 D-Arabinitol | − |
| 46 L-Arabinitol | + |
| 47 Gluconate | − |
| 48 2-Keto-Gluconate | − |
| 49 5-Keto-Gluconate | − |

The molecular biology method of 18S rRNA gene sequencing was adopted to identify the above *Candida ethanolica* B-JJ1, whose gene sequences are shown in SEQ.ID.NO.1, and the 16s rRNA gene sequencing method was adopted to identify the were sequence of *Lentilactobacillus buchneri* B-JR1, *Lactobacillus paracasei* B-JR2, *Lactobacillus zeae* B-JR4, *Lactobacillus plantarum* B-JR5 and *Lactobacillus chiayiensis* B-JR6, and their gene sequences are shown in SEQ.ID.NO.2, SEQ.ID.NO.3, SEQ.ID.NO.4, SEQ.ID.NO.5, and SEQ.ID.NO.6, respectively.

The invention can be purified and separated according to the actual needs, and then mixed and formulated into a combination of bacteria with different properties, for example, the yeast and lactic acid bacteria combination of the invention can include *Candida ethanolica* B-JJ1, *Lentilactobacillus buchneri* B-JR1, *Lactobacillus chiayiensis* B-JR6; or *Candida ethanolica* B-JJ1, *Lentilactobacillus buchneri* B-JR1, *Lactobacillus paracasei* B-JR2, *Lactoba-*

*cillus chiayiensis* B-JR6; or *Candida ethanolica* B-JJ1, and the lactic acid bacteria comprise *Lentilactobacillus buchneri* B-JR1, *Lactobacillus paracasei* B-JR2, *Lactobacillus zeae* B-JR4, *Lactobacillus chiayiensis* B-JR6.

The specific operation can be obtained after the separation and purification of the six species including *Candida ethanolica* B-JJ1, *Lentilactobacillus buchneri* B-JR1, *Lactobacillus paracasei* B-JR2, *Lactobacillus zeae* B-JR4, *Lactobacillus plantarum* B-JR5 and *Lactobacillus chiayiensis* B-JR6 prepared in step (9) of embodiments 1 to 3 in accordance with the conventional method in the art, and then expanded separately according to the demand After culturing, then mixed culture is carried out to cultivate different combined bacteria.

The combined bacteria provided by invention can also be directly adopted from the combined bacteria obtained in step (9) of embodiments 1 to 3.

Embodiment 4

A bio-enzyme preparation, prepared from the fermentation products of the yeast and the lactic acid bacteria combined bacteria, and the preparation process are as follows:

(1) Culture medium preparation: taking 30 parts of mashed potato powder, 30 parts of wheat germ, 20 parts of glutinous rice, 10 parts of sorghum rice, 10 parts of buckwheat as the main ingredients for preparation;

(2) Inoculation of combined bacteria yeast and lactic acid bacteria onto the medium for fermentation; wherein the yeast and lactic acid bacteria combination comprise *Candida ethanolica* B-JJ1, *Lentilactobacillus buchneri* B-JR1, *Lactobacillus chiayiensis* B-JR6;

(3) adjusting the humidity of the culture medium after inoculation in step (2) to ensure that the medium remain water seeping when hold by hand and the whole medium is kept moist and breathable;

(4) processing the aerobic fermentation of the medium in step (3) for over 48 hours until the medium uniformly appears white and milky white bacterial plaque to be visible with the naked eye, and then transferring the medium into the fermenter; the solid fermentation can occupy one third of the fermenter; to enable the medium fermentations into the tank to continue aerobic culture in the tank until the oxygen in the tank is depleted and enters the anaerobic fermentation state;

(5) When step (4) continues fermentation until the solid state fermentation reaches saturation, adding sterile water and stirring to enter the liquid state fermentation stage, making sure that there is at least ⅕ space in the fermenter, and then carrying out aerobic activation and incubation for more than 72 hours until the surface of the liquid state fermentation is densely covered with white or milky white bacteria plaque, and then entering anaerobic fermentation again when the aerobic fermentation has depleted the oxygen in the fermenter;

(6) When the bacterial plaque on the surface of the liquid fermentation in step (6) is in folding state, the middle and upper layers of clear liquid appear golden yellow, clear and transparent, and the solid fermentation to liquid fermentation process is regarded as full complement, when the bottom layer of solid fermentation and the middle layer of liquid are clearly layered and not sticky, and the fermentation product obtained is the bio-enzyme preparation.

Embodiment 5

A bio-enzyme preparation, prepared from the fermentation products of the yeast and lactic acid bacteria combination, and the preparation process are as follows:

(1) Culture medium preparation: taking 30 parts of mashed potato powder, 30 parts of wheat germ, 20 parts of glutinous rice, 10 parts of sorghum rice, 10 parts of buckwheat as the main ingredients for preparation;

(2) Inoculation of yeast and lactic acid bacteria combination onto the medium for fermentation; wherein the yeast and lactic acid bacteria combination comprise *Candida* ethanolica B-JJ1, *Lentilactobacillus buchneri* B-JR1, *Lactobacillus paracasei* B-JR2, *Lactobacillus chiayiensis* B-JR6;

(3) Adjusting the humidity of the culture medium after inoculation in step (2) to ensure that the medium remain water seeping when hold by hand and the whole medium is kept moist and breathable;

(4) Processing the aerobic fermentation of the medium in step (3) for over 48 hours until the medium uniformly appears white and milky white bacterial plaque to be visible with the naked eye, and then transferring the medium into the fermenter; the solid fermentation can occupy one third of the fermenter; to enable the medium fermentations into the tank to continue aerobic culture in the tank until the oxygen in the tank is depleted and enters the anaerobic fermentation state;

(5) When step (4) continues fermentation until the solid state fermentation reaches saturation, adding sterile water and stirring to enter the liquid state fermentation stage, making sure that there is at least ⅕ space in the fermenter, and then carrying out aerobic activation and incubation for more than 72 hours until the surface of the liquid state fermentation is densely covered with white or milky white bacteria plaque, and then entering anaerobic fermentation again when the aerobic fermentation has depleted the oxygen in the fermenter;

(6) When the bacterial plaque on the surface of the liquid fermentation in step (6) is in folding state, the middle and upper layers of clear liquid appear golden yellow, clear and transparent, and the solid fermentation to liquid fermentation process is regarded as full complement, when the bottom layer of solid fermentation and the middle layer of liquid are clearly layered and not sticky, and the fermentation product obtained is the bio-enzyme preparation.

Embodiment 6

A bio-enzyme preparation, prepared from the fermentation products of the yeast and lactic acid bacteria combination, and the preparation process are as follows:

(1) Culture medium preparation: taking 30 parts of mashed potato powder, 30 parts of wheat germ, 20 parts of glutinous rice, 10 parts of sorghum rice, 10 parts of buckwheat as the main ingredients for preparation;

(2) Inoculation of yeast and lactic acid bacteria combination onto the medium for fermentation; wherein the yeast and lactic acid bacteria combination comprise *Candida ethanolica* B-JJ1, *Lentilactobacillus buchneri* B-JR1, *Lactobacillus paracasei* B-JR2, *Lactobacillus zeae* B-JR4, *Lactobacillus plantarum* B-JR5 and *Lactobacillus chiayiensis* B-JR6;

(3) Adjusting the humidity of the culture medium after inoculation in step (2) to ensure that the medium remain water seeping when hold by hand and the whole medium is kept moist and breathable;

(4) Processing the aerobic fermentation of the medium in step (3) for over 48 hours until the medium uniformly appears white and milky white bacterial plaque to be visible with the naked eye, and then transferring the medium into the fermenter; the solid fermentation can occupy one third of the fermenter; to enable the medium fermentations into the tank to continue aerobic culture in the tank until the oxygen in the tank is depleted and enters the anaerobic fermentation state;

(5) When step (4) continues fermentation until the solid state fermentation reaches saturation, adding sterile water and stirring to enter the liquid state fermentation stage, making sure that there is at least ⅕ space in the fermenter, and then carrying out aerobic activation and incubation for more than 72 hours until the surface of the liquid state fermentation is densely covered with white or milky white bacteria plaque, and then entering anaerobic fermentation again when the aerobic fermentation has depleted the oxygen in the fermenter;

(6) When the bacterial plaque on the surface of the liquid fermentation in step (6) is in folding state, the middle and upper layers of clear liquid appear golden yellow, clear and transparent, and the solid fermentation to liquid fermentation process is regarded as full complement, when the bottom layer of solid fermentation and the middle layer of liquid are clearly layered and not sticky, and the fermentation product obtained is the bio-enzyme preparation.

Embodiment 7

A biological preservative prepared from the bio-enzyme preparation of embodiment 4 to embodiment 6.

Embodiment 8

The bio-enzyme preparation of embodiment 4 to embodiment 7 is applied directly as a biological preservative.

Embodiment 9

The bio-enzyme preparation prepared in embodiment 6 is inactivated by heating, and the supernatant of the ferment is extracted to produce a bio-enzyme preparation, which is applied directly as a biological preservative.

Embodiment 10

The bio-enzyme preparation obtained in embodiment 8 is applied as a biological preservative and freshness preservative in the following way:

Creating a microclimate environment for colony dominance, and placing the material to be preserved in the environment. The method is suitable for preserving and antioxidation of large area and multi-mass material: for example, a closed storage room can be thoroughly sterilized, and then the preserved items can be evenly spread on the shelf, with layers, without stacking and squeezing. After the storage is finished, taking the active enzyme preparation and covering it with detailed spray at one time, until the humidity in the storage room is above 90%, and the temperature is kept in the range from below room temperature to above 0° C. in closed storage to avoid infection of miscellaneous bacteria;

Or wrapping, dipping, smearing and so on, which is suitable for the specimen production of human body and animal body.

Or one-time dipping and spraying treatment, which is suitable for preserving the freshness of fruits and vegetables.

Embodiment 10

Figure 7:
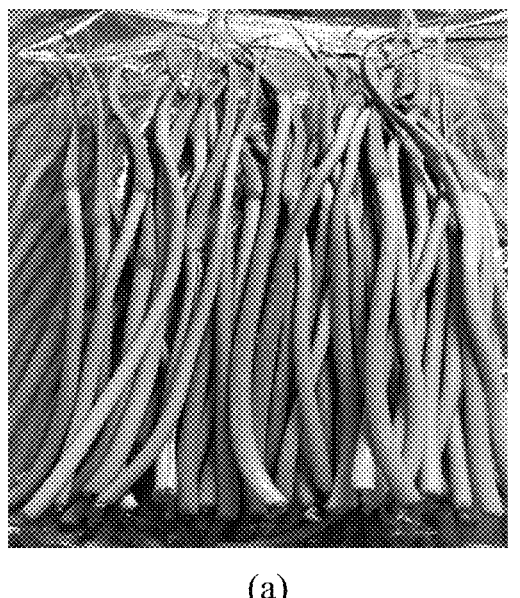
FIG. 7 is a photograph showing the garlic sprout freshness experiment by application of the bio-enzyme preparation of embodiment 10 provided by the invention.
Figure 7:
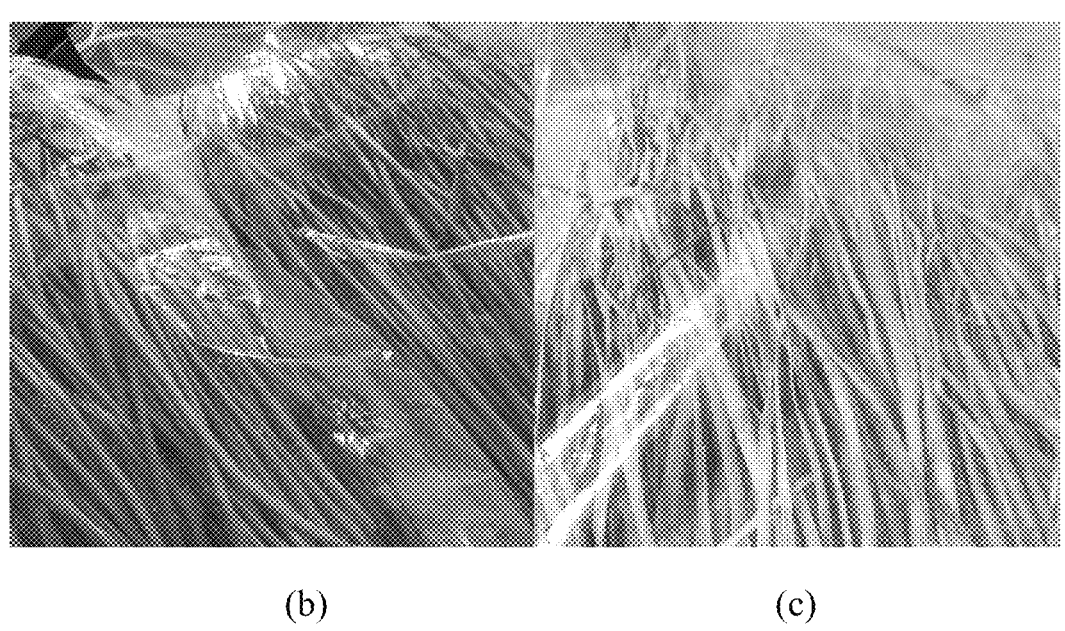

The embodiment applied the preservative prepared in embodiment 9 to preserve garlic sprout:

The specific operation is as follows: a batch of purchased garlic sprout is divided into two groups, and FIG. 7 (a) shows the state of garlic sprout before the experiment; one group of garlic sprout after grouping is placed in the preservation bag after spraying the fermentation substrate on its surface, and the other group is placed in the preservation bag directly without any treatment, and then the two groups of preservation bags are placed at room temperature for two months; after two months, FIG. 7 (b) is a photo of garlic sprout treated with preservative, and FIG. 7 (c) is a photo of untreated garlic sprout. Comparing the state of garlic sprouts in FIG. 7 (b) and FIG. 7 (c), it is obvious that the garlic sprouts treated with preservative of the invention have fresh color, sufficient water, good shape, and almost no appearance of drying or yellowing, while the untreated ones have serious water loss and appears large areas of yellowing, dryness and resulting in other shapes.

Embodiment 11

Figure 8:
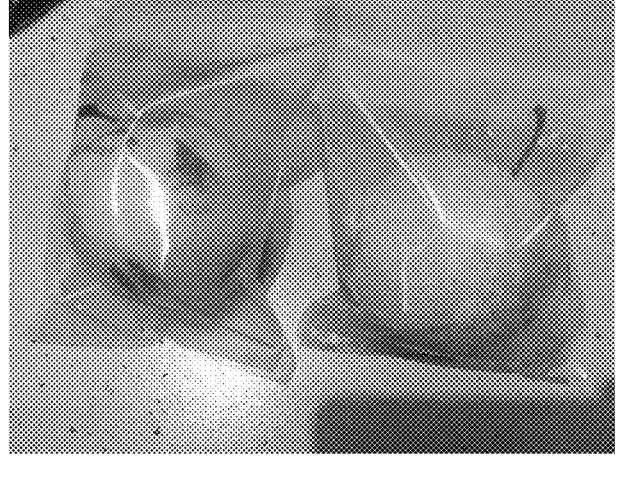
FIG. 8 is a photograph showing the pear freshness experiment by application of the bio-enzyme preparation of embodiment 11 provided by the invention.
Figure 8:
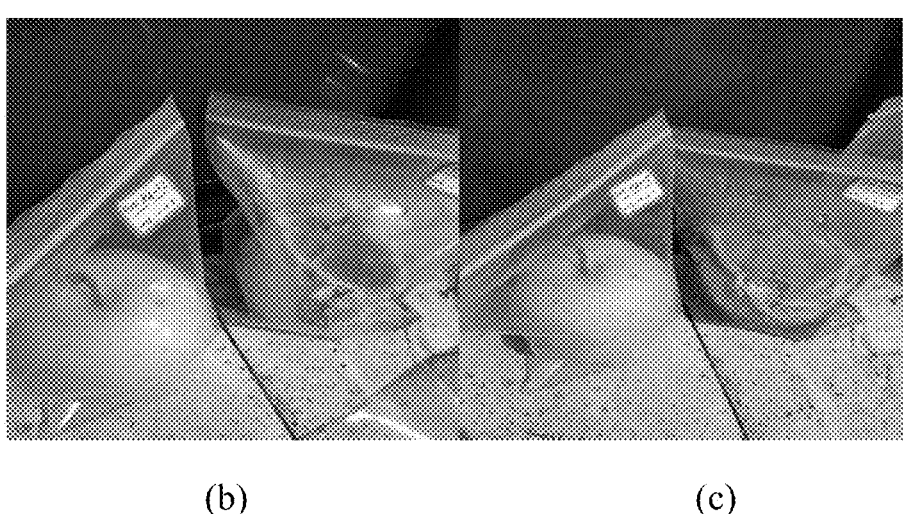

The embodiment applies the preservative prepared in embodiment 9 to preserve the pears: Choosing the same group of two pears, and the state before the experiment is shown in FIG. 8 (a), one of the pears is placed in the preservation bag after spraying the preservative on its surface, and the other is placed directly in the preservation bag without any treatment, and then the two groups of preservation bags are placed at room temperature for preservation; the state of the two pears after six months is shown in FIG. 8 (b), and the state of the two pears after one year is shown in FIG. 8 (c), where the left side of FIG. 8 (b) and FIG. 8 (c) is the pear after treatment, and the right side is the pear without treatment. It is obvious from FIG. 8 (b) and FIG. 8 (c) that the effect of the invention on the preservation of the fruit freshness, since the left side can still keep the color fresh, full of water and good shape after one year with treatment, while the untreated one has been corrupted into water.

Embodiment 12

Figure 9:
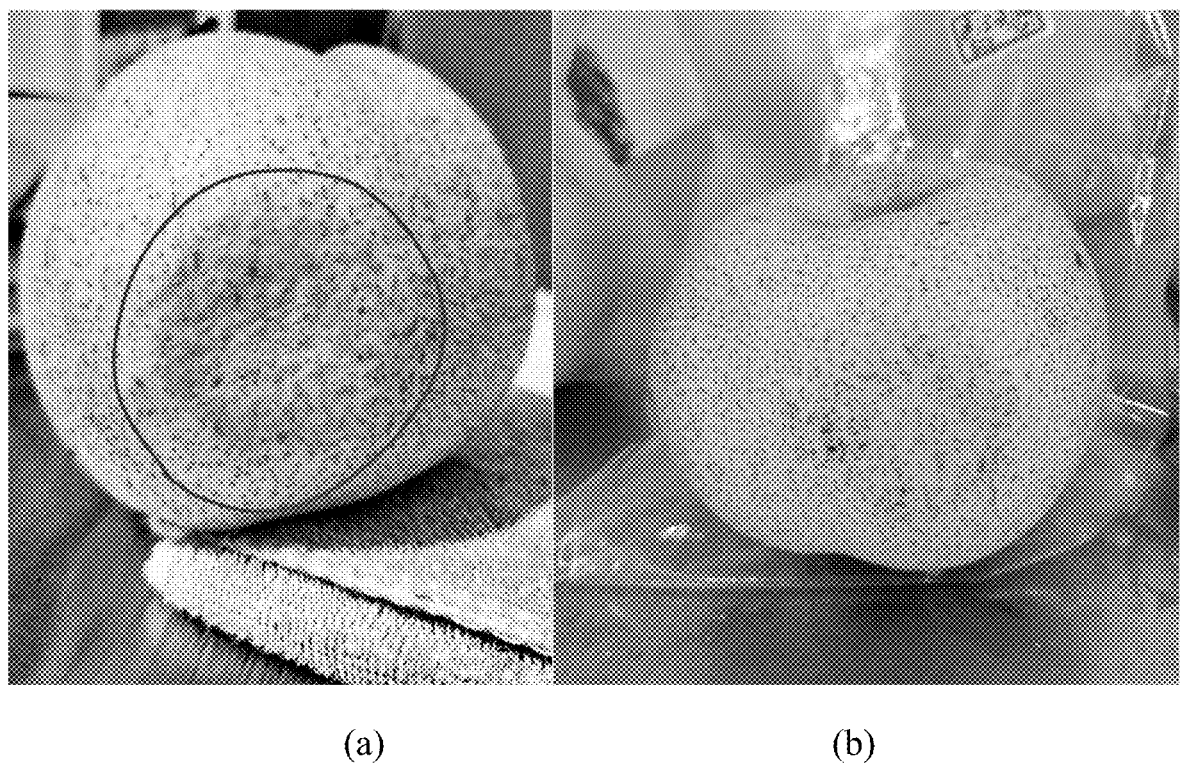
FIG. 9 is a photograph showing the injured pears freshness experiment by application of the bio-enzyme preparation of embodiment 12 provided by the invention.

The embodiment applies the preservative prepared in embodiment 9 to preserve the injured pears:

FIG. 9 (a) shows the pear which has obvious dent after impact before the experiment, then spraying the preservative of embodiment 7 on the surface of the pear which has dent, placing it into the preservation bag and keeping it at room temperature; After 9 months, the state of the pear is shown in FIG. 9 (b), and comparing the state of the same pear with 9 months intervals in FIG. 9 (a) and FIG. 9 (b), it is obvious that after 9 months, the pear has self-recovery at its impact damage, and the dent is not obvious; therefore it can be concluded that the preservative of the invention not only has excellent antiseptic preservation effect, but also has strong repair effect for the broken cell tissue.

Embodiment 13

Figure 10:
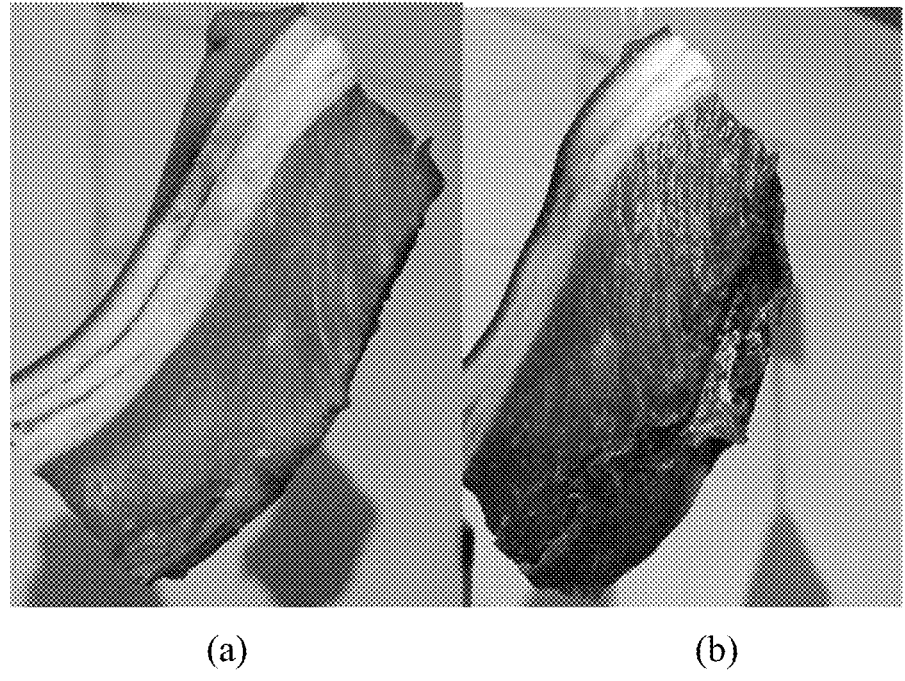
FIG. 10 is a photograph showing freshness experiment of fresh pork by application of the bio-enzyme preparation of embodiment 13 provided by the invention.

The embodiment applies the preservative prepared in embodiment 9 to preserve the fresh pork:

Taking fresh pork from the market shown in FIG. 10 (*a*), the surface of the fresh pork was evenly sprayed with preservative and kept at room temperature for 1 month; referring to FIG. 10 (*b*), the comparison of the photos of pork before and after preservation of this embodiment, it can be seen that except for some surface performance of the pork with some water loss and dryness (which is normal phenomenon for water evaporation, due to the lack of airtight preservation), the other color and luster is normal, and without any peculiar smell.

Embodiment 14

Figure 11:
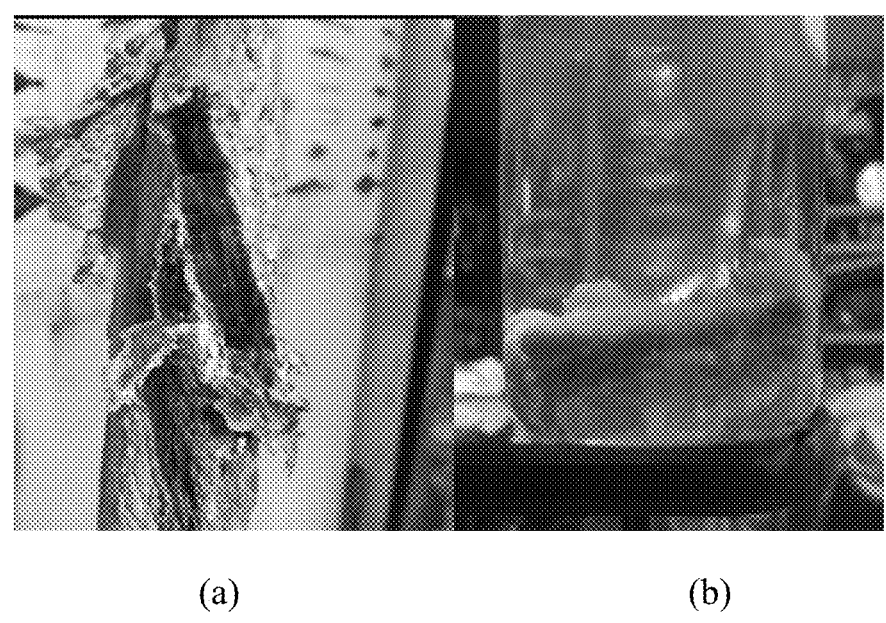
FIG. 11 is a photograph showing the freshness experiment of fresh pork by application of the bio-enzyme preparation of embodiment 14 provided by the invention.

The embodiment applies the preservative prepared in embodiment 9 to preserve fresh meat:

Taking fresh pork from the market, spraying the surface of pork with preservative evenly and then placing it at room temperature for air-drying, after its surface is completely air-dried, cutting the surface to observe its internal condition as shown in FIG. 11 (*a*), and it is obvious that although the surface is in air-drying and turning white, the inside of the meat is still fresh in color, and it is also obvious that its water has been evaporated, showing the drying phenomenon; after the air-dried meat is completely immersed in water, it can be restored to the fresh meat state at room temperature for about two hours, as shown in FIG. 11 (*b*), from which it can be seen that the cells of pork still hold activity and can absorb water again, and thus some parts of pork appear in good state.

Embodiment 15

Figure 12:
FIG. 12 is a photograph showing the freshness experiment of fresh pig's head by application of the bio-enzyme preparation of embodiment 15 provided by the invention.

The embodiment applies the preservative prepared in embodiment 9 to preserve fresh pigs head:

Taking fresh pig head immersed in above preservative for 24 hours, taking out and placing on a permeable shelf to drain the enzyme preparation and other water until the surface and the cross section of the pig's head is dry to ensure that there is no residual preservative and other water at the mouth, trachea, brain stem and under the tongue root; and then taking the pig's head for airtight storage for 4 years, and the state of the pig's head after 4 years is referred to the FIG. 12.

Embodiment 16

Figure 13:
FIG. 13 is a photograph showing the freshness experiment of fresh shrimp by application of the bio-enzyme preparation of embodiment 16 provided by the invention.

The embodiment applies the preservative prepared in embodiment 9 to preserve fresh shrimp:

Taking freshwater shrimp and placing them in a jar with preservation solution, and then storing them airtight for 3 months referring to the FIG. 13. It is evident from FIG. 13 that even after 4 months, the color of the shrimp appeared no changes, such as the redness caused by spoilage, and the color was not significantly different from that of fresh shrimp.

Embodiment 16

The embodiment applies the preservative prepared in embodiment 9 to preserve fresh shrimp:

Taking freshwater shrimp and placing them in a jar with preservation solution, and then storing them airtight for 3 months referring to the FIG. 13. It is evident from FIG. 13 that even after 4 months, the color of the shrimp appeared no changes, such as the redness caused by spoilage, and the color was not significantly different from that of fresh shrimp.

Embodiment 17

Figure 14:
FIG. 14 is a photograph showing the anti-mould experiment of the bio-enzyme preparation of embodiment 17 provided by the invention.

The embodiment applies the anti-mould experiments of the preservative prepared in embodiment 9, and the specific experiments are as follows:

Taking mashed potato powder, with the addition of preservative water to moisten and forming into the shape of a ball; then using water without the addition of preservative to moisten the mashed potato powder and forming into the shape of a ball for comparison; the two mashed potato powder formed into the shape of ball are placed at room temperature for 3 days; referring to FIG. 14, the left side of FIG. 14 is not added to the preservative, the right side is added with preservative, and it is obvious that the invention has a good effect of anti-mould after comparison.

Embodiment 18

Figure 15:
FIG. 15 is a photograph showing the saccharification inhibition experiment of the bio-enzyme preparation of embodiment 18 provided by the invention.
Figure 16:
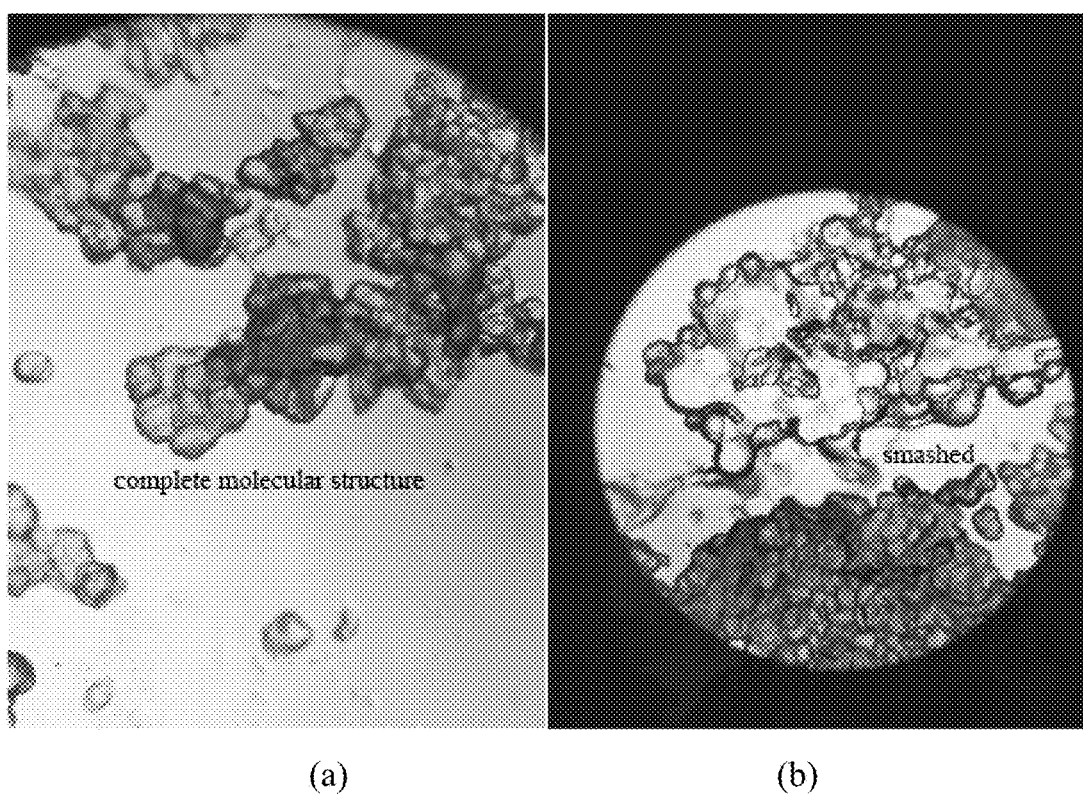
FIG. 16 is a microscopic photograph showing the molecules of mashed potato powder by the bio-enzyme preparation of embodiment 16 provided by the invention.

The embodiment applies the uninactivated bio-enzyme preparation in embodiment 6 for saccharification inhibition experiment of mashed potato ball:

Taking mashed potato powder, with the addition of preservative water to moisten and forming into the shape of a ball; then using water without the addition of preservative to moisten the mashed potato powder and forming into the shape of a ball for comparison; placing the two groups of mashed potato balls under the same conditions and leave them at room temperature for 72 hours; the results are shown in FIG. 15, where the top left corner of FIG. 15 shows the mashed potato balls without the treatment of bio-enzymes preparation, and the bottom right corner shows the mashed potato balls with the treatment of bio-enzymes preparation. It is obvious that the shape, color and taste of the mashed potato balls with the application of preservatives did not show any obvious changes, and the cell structure of the microscopic image was found to be complete referring to the FIG. 16*a*, with a slight dry skin on the surface due to dehydration; in contrast, the control group was soft and sticky with a sour smell, and the microscopic images showed that the molecular structure was broken apart and the cells were in a shell-like state referring to the FIG. 16*b*. It is obvious that the bio-enzyme preparation prepared by the invention has the effect of inhibiting saccharification, and the analysis illustrate that the slowing down of the saccharification process of the organism can be achieved through the inhibition of a-amylase activity.

The invention and the embodiments thereof are described hereinabove, and this description is not restrictive. What is shown above is only the principles and the preferred embodiments of the invention, and the actual structure is not limited thereto. In summary, any equivalent structures or equivalent process transformations made by using the specifications and the attaching drawings of the invention, or direct or indirect applications to other related technical fields, shall all fall within the protection scope of the invention.

The invention claimed is:

1. A method for preparing bio-enzyme preparation, wherein comprises the following steps:

(1) selecting a yeast and lactic acid bacteria combination as a culture, the yeast and lactic acid bacteria combination comprises *Candida ethanolica* B-JJ1, *Lentilactobacillus buchneri* B-JR1, *Lactobacillus paracasei* B-JR2, *Lactobacillus zeae* B-JR4, *Lactobacillus plantarum* B-JR5 and *Lactobacillus chiayiensis* B-JR6; the *Candida ethanolica* B-JJ1 with the deposit number: CCTCC NO: M2021136;

the *Lentilactobacillus buchneri* B-JR1 with the deposit number: CCTCC NO: M2021132;

the *Lactobacillus paracasei* B-JR2 with the deposit number: CCTCC NO: M2021133;

the *Lactobacillus zeae* B-JR4 with the deposit number: CCTCC NO: M2021135;

the *Lactobacillus plantarum* B-JR5 with the deposit number: CCTCC NO: M2021501;

the *Lactobacillus chiayiensis* B-JR6 with the deposit number: CCTCC NO: M2021502;

(2) preparation and inoculation of a medium of the culture: the medium is prepared with mashed potato powder, wheat germ and glutinous rice as main ingredients; the medium is steamed after adding water and stirring evenly, and the preparation of the medium has been completed when temperature of the medium is cooled to below 45° C. in aseptic conditions; homogeneously mixing the prepared medium with the culture;

(3) adjusting humidity of the culture medium after inoculation in step (2) to ensure that there are water seeps on the medium and the whole medium is kept moist and breathable;

(4) processing aerobic fermentation of the medium in step (3) until the medium uniformly appears white and milky white bacterial plaque to be visible with the naked eye, and then transferring the medium into a fermenter; to close all channels of the fermenter to enable the medium fermentations into the fermenter to continue aerobic culture in the fermenter until the oxygen in the fermenter is depleted and enters anaerobic fermentation state;

(5) when there is no pressure change in the fermenter, solid-state fermentation enters into saturation fermentation, and there is a strong fermentation fragrance when opening the tank, with abundant mycelium covering the surface of the solid medium to be visible with the naked eye; taking the fermentation products for testing, and the total number of viable yeast is $6.4\times10^4$-$5.9\times10^5$ cfu/ml; the total number of viable lactic acid bacteria is $4\times10^8$-$5.1\times10^9$ cfu/ml; and at this time the solid fermentation process has reached saturation point, and then enters the liquid fermentation stage;

(6) adding the solid-state fermentation in the step (5) to sterile water and stirring thoroughly, and carrying out aerobic activation and cultivation until the surface of the liquid ferment is densely covered with white or milky white bacterial plaque; to close all channels of the fermenter and again allow the fermentation to gradually deplete oxygen and enter into the anaerobic fermentation process;

(7) when the bacterial plaque on the surface of the liquid fermentation in step (6) is in folding state, the middle and upper layers of clear liquid appear golden yellow, clear and transparent, and the solid fermentation to liquid fermentation process is regarded as full complement, when the bottom layer of solid fermentation and the middle layer of liquid are clearly layered and not sticky, and the fermentation product obtained is the bio-enzyme preparation.

2. A method for preparing the bio-enzyme preparation according to the claim 1, wherein further comprises the following steps:

(8) heating the fermentation substrate obtained in step (7) and extracting the supernatant of the ferment, to obtain the inactivated bio-enzyme preparation.

* * * * *